(12) United States Patent
Childs et al.

(10) Patent No.: US 10,106,620 B2
(45) Date of Patent: Oct. 23, 2018

(54) BLOCKING CD38 USING ANTI-CD38 F(AB')2 TO PROTECT NK CELLS

(71) Applicants: The United States of America, as represented by the Secretary, Dept. of Health and Human Services, Bethesda, MD (US); Janssen Biotech, Inc., Spring House, PA (US)

(72) Inventors: Richard W. Childs, Rockville, MD (US); Maria Berg, Bethesda, MD (US); Luis Espinoza Calderon, Bethesda, MD (US); Kate Sasser, Spring House, PA (US); Ricardo Attar, Spring House, PA (US)

(73) Assignees: The United States of America, as represented by the Secretary, Department of Health and Human Services, Washington, DC (US); Janssen Biotech, Inc., Spring House, PA (US)

( * ) Notice: Subject to any disclaimer, the term of this patent is extended or adjusted under 35 U.S.C. 154(b) by 123 days.

(21) Appl. No.: 15/319,344

(22) PCT Filed: Jun. 15, 2015

(86) PCT No.: PCT/US2015/035832
§ 371 (c)(1),
(2) Date: Dec. 15, 2016

(87) PCT Pub. No.: WO2015/195556
PCT Pub. Date: Dec. 23, 2015

(65) Prior Publication Data
US 2018/0208669 A1 Jul. 26, 2018

Related U.S. Application Data

(60) Provisional application No. 62/012,864, filed on Jun. 16, 2014.

(51) Int. Cl.
*C07K 16/00* (2006.01)
*C07K 16/28* (2006.01)
*A61P 35/02* (2006.01)
*A61P 37/00* (2006.01)

(52) U.S. Cl.
CPC .......... *C07K 16/2896* (2013.01); *A61P 35/02* (2018.01); *A61P 37/00* (2018.01); *C07K 2317/21* (2013.01); *C07K 2317/54* (2013.01); *C07K 2317/732* (2013.01)

(58) Field of Classification Search
None
See application file for complete search history.

(56) References Cited

U.S. PATENT DOCUMENTS 7,829,673 B2    11/2010   De Weers et al.

FOREIGN PATENT DOCUMENTS

| EP | 1914242 A1 | 4/2008 |
| EP | 2567976 A2 | 3/2013 |
| WO | WO 2005/103083 A2 | 11/2005 |
| WO | WO 2008/047242 A2 | 4/2008 |
| WO | WO 2012/041800 A1 | 4/2012 |

OTHER PUBLICATIONS

De Weers, et al., "Daratumumab, a novel therapeutic human CD38 monoclonal antibody, induces killing of multiple myeloma and other hematological tumors," *The Journal of Immunology*, vol. 186, No. 3, pp. 1840-1848, 2011.
Sconocchia et al., "CD38 triggers cytotoxic responses in activated human natural killer cells," *Blood*, vol. 94, No. 11, pp. 3864-3871, 1999.
Srivastava, et al., "Natural killer cell immunotherapy for cancer: a new hope," *Cytotherapy*, vol. 10, No. 8, pp. 775-783, 2008.
Stevenson, et al., "Preliminary studies for an immunotherapeutic approach to the treatment of human myeloma using chimeric anti-DC38 antibody," *Blood*, vol. 77, No. 5, pp. 1071-1079, 1991.
Taussig et al., "Anti-CD38 antibody-mediated clearance of human repopulating cells masks the heterogeneity of leukemia-initiating cells," *Blood*, vol. 112, No. 3, pp. 568-575, 2008.
van der Veer et al., "The therapeutic human CD38 antibody daratumumab improves the anti-myeloma effect of newly emerging multi-drug therapies," *Blood Cancer Journal*, vol. 1:e41, 2011 (3 pages).

*Primary Examiner* — Sean E Aeder
(74) *Attorney, Agent, or Firm* — Klarquist Sparkman, LLP

(57) ABSTRACT

Provided herein are methods of inhibiting growth or proliferation of cells expressing CD38 by contacting the CD38-expressing cells with 1) NK cells bound to an anti-CD38 F(ab')$_2$ fragment and 2) an anti-CD38 antibody, in either order or simultaneously. Also provided herein are methods of treating or inhibiting a hyperproliferative disorder or an autoimmune disorder in a subject by administering to the subject 1) NK cells bound to an anti-CD38 F(ab')$_2$ fragment and 2) an anti-CD38 antibody, in either order or simultaneously.

27 Claims, 22 Drawing Sheets

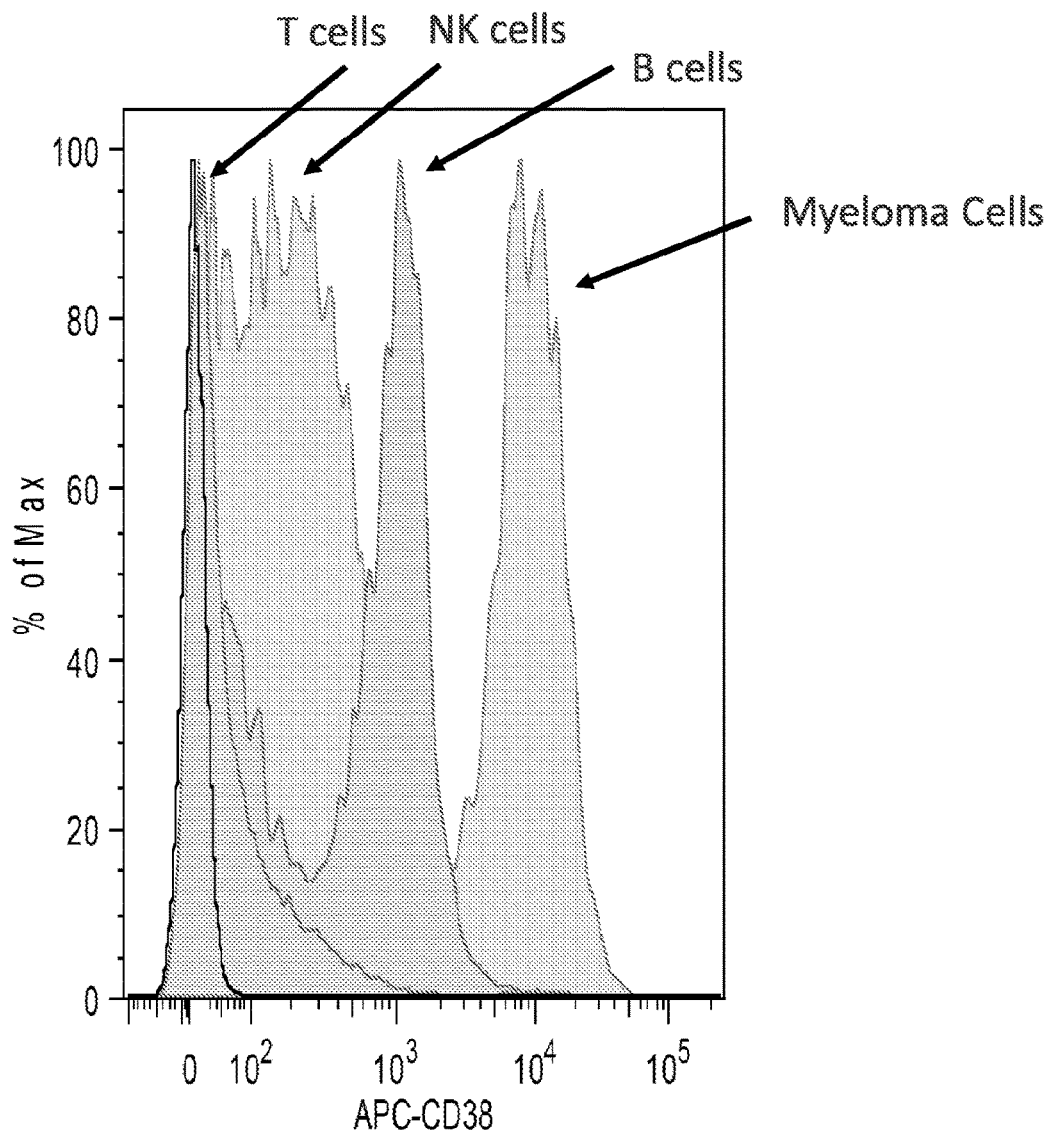

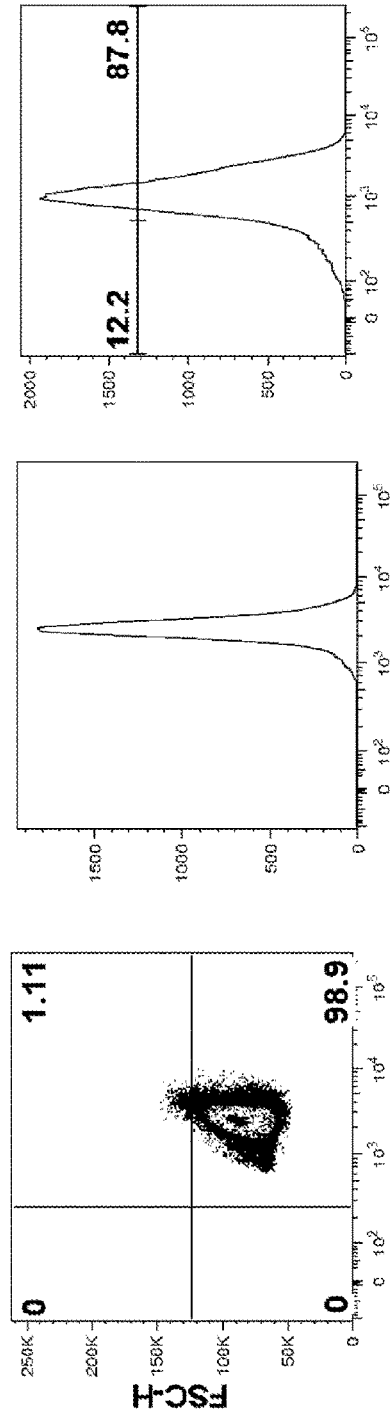
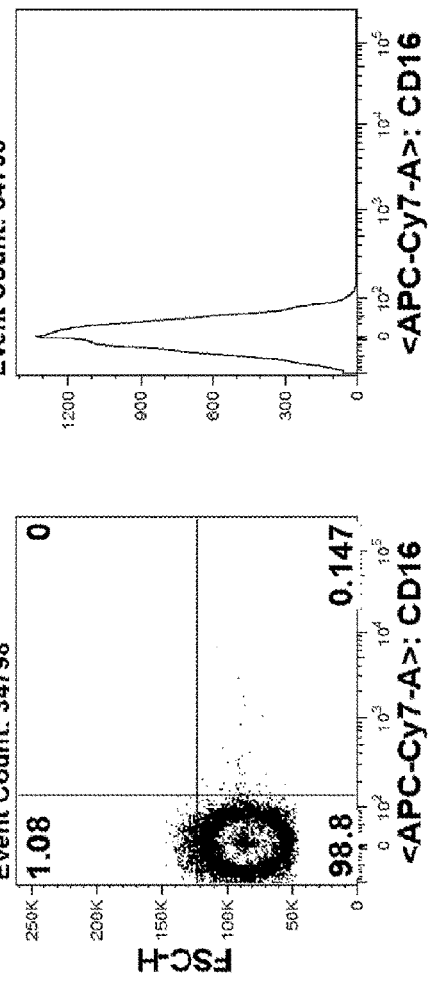
FIG. 4A
FIG. 4B

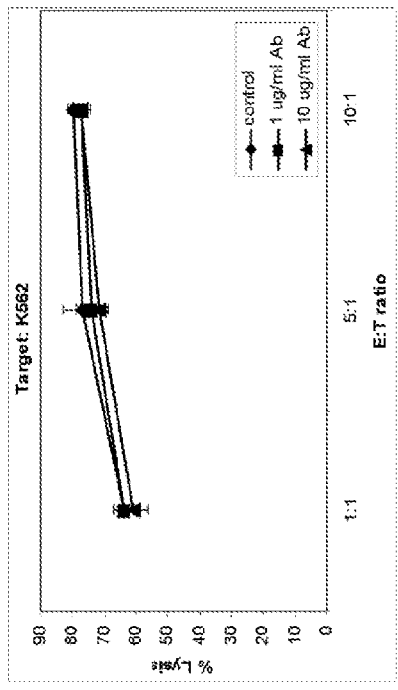
FIG. 7A
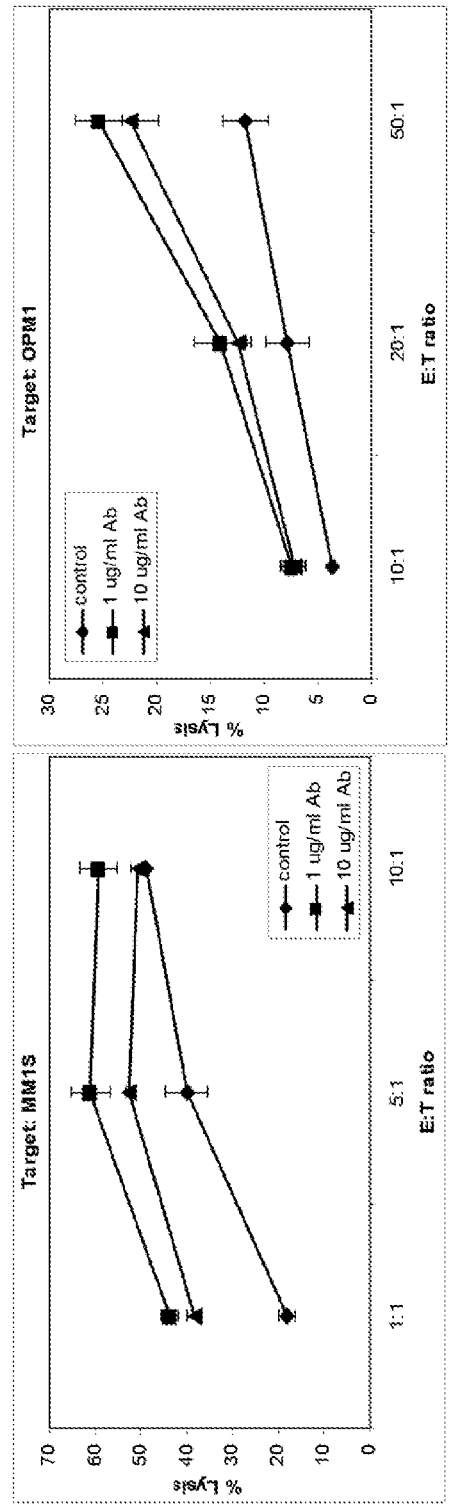
FIG. 7B
FIG. 7C

FIG. 8A Control　　+ Daratumumab 10ug/ml
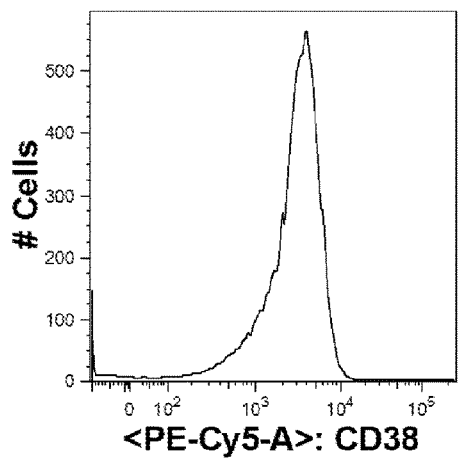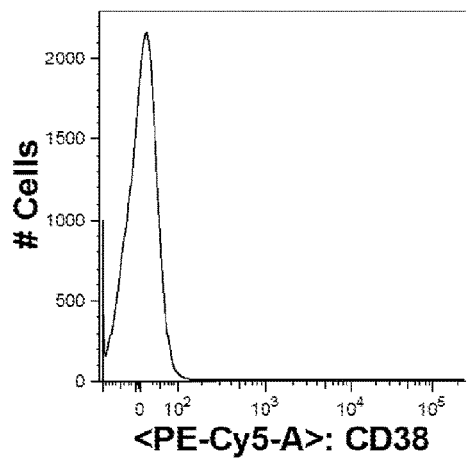
FIG. 8B
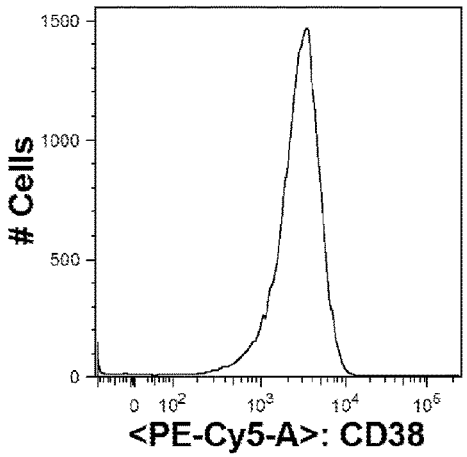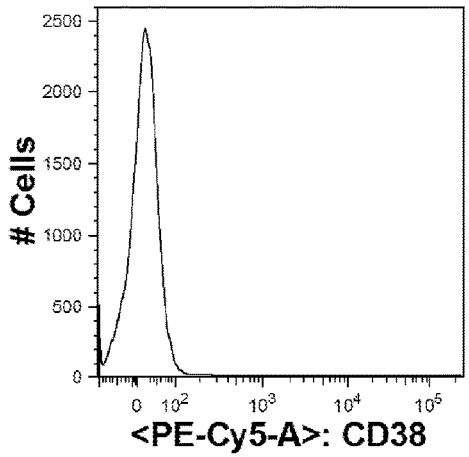

FIG. 9A Control        + Daratumumab 10ug/ml
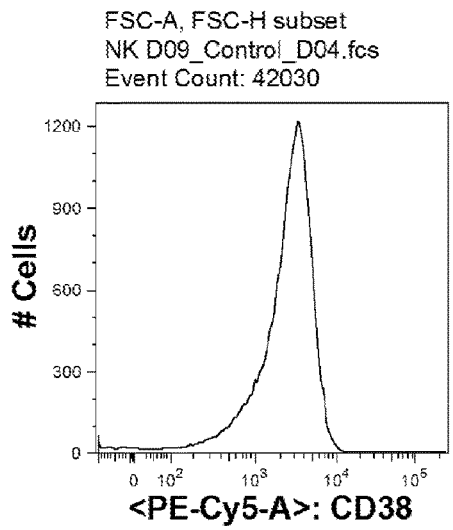 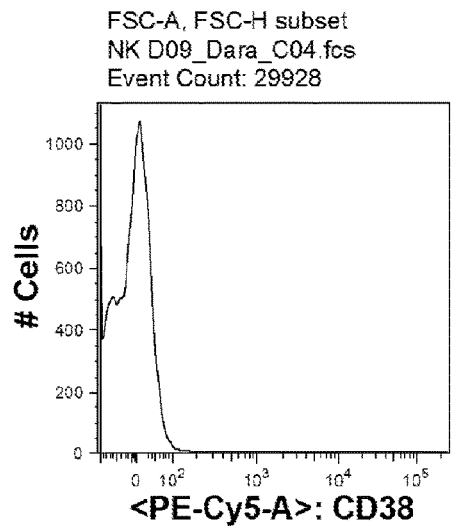
FIG. 9B
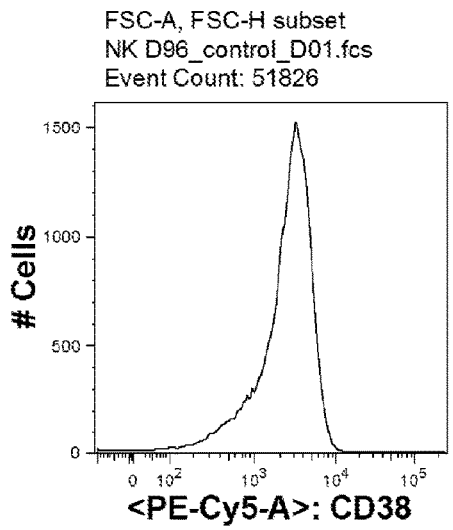 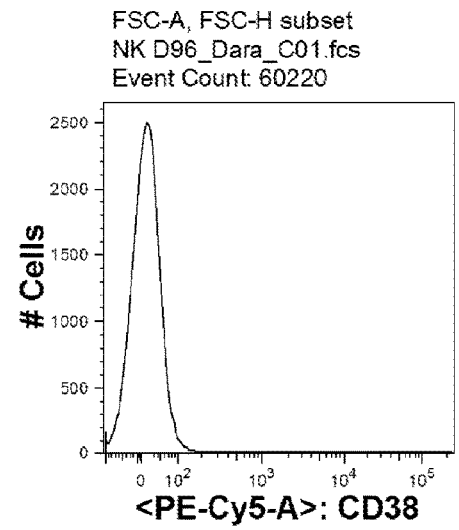

Control
FIG. 10A
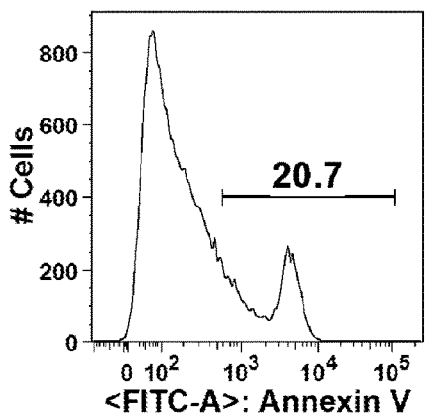
Daratumumab
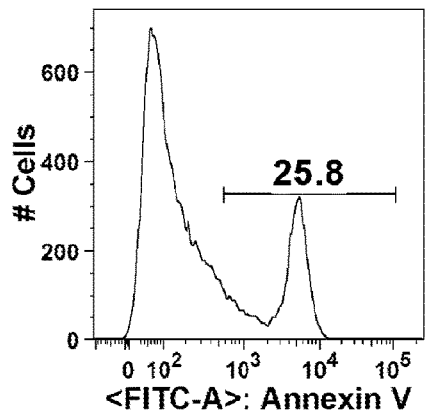
FIG. 10B
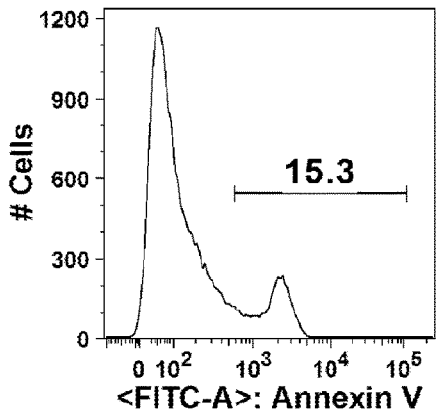
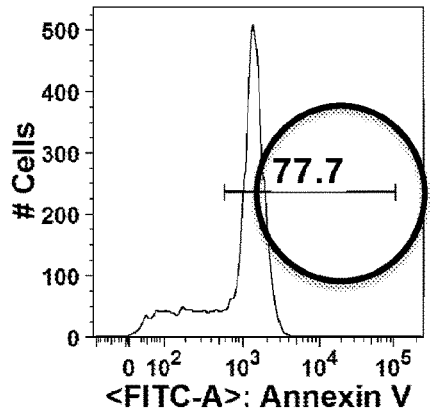

FIG. 11A U226 cells vs NK D0464 (low affinity IgG binding)
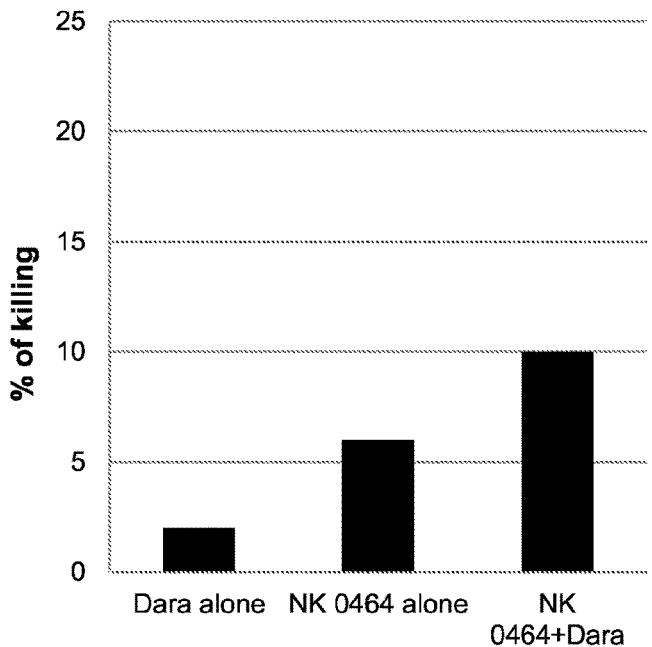
FIG. 11B U226 cells vs NK D1096 (High affinity IgG binding)
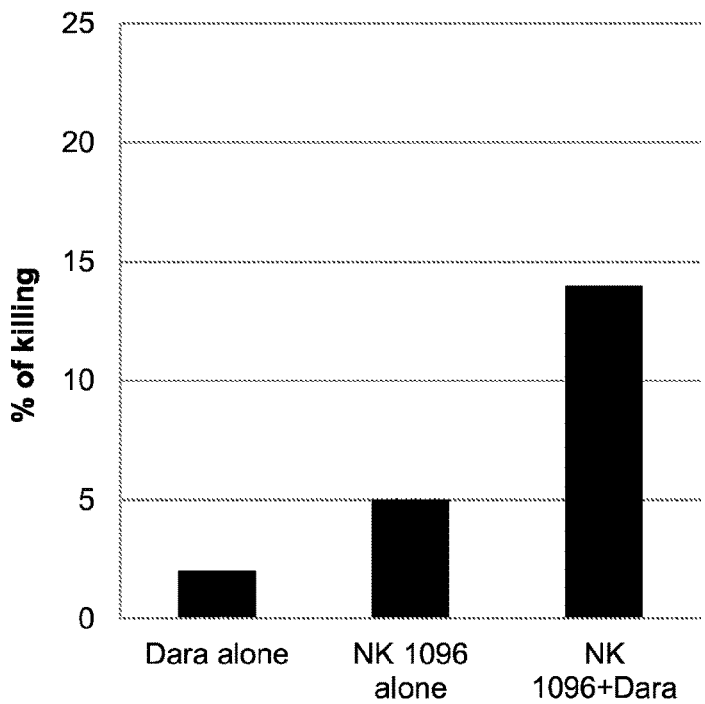

FIG. 18A
FSC-A, FSC-H subset
Dara_UNT_E05.fcs
Event Count: 16285
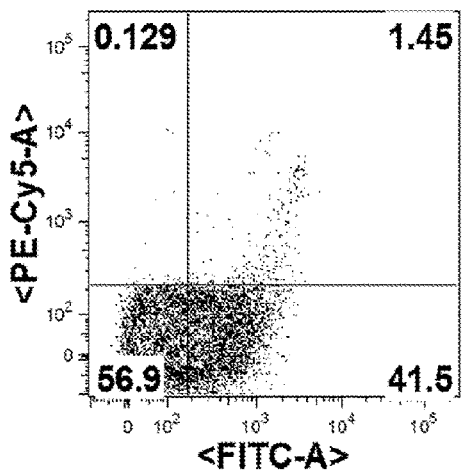
FIG. 18B
FSC-A, FSC-H subset
Dara_F(ab)2 OFA_E08.fcs
Event Count: 17700
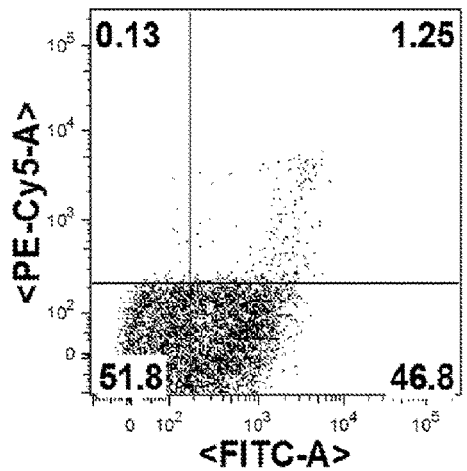
FSC-A, FSC-H subset
Dara_F(ab)2 Dara 5_E06.fcs
Event Count: 12341
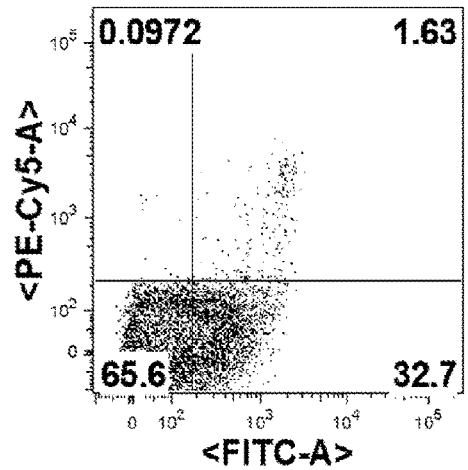
FIG. 18C

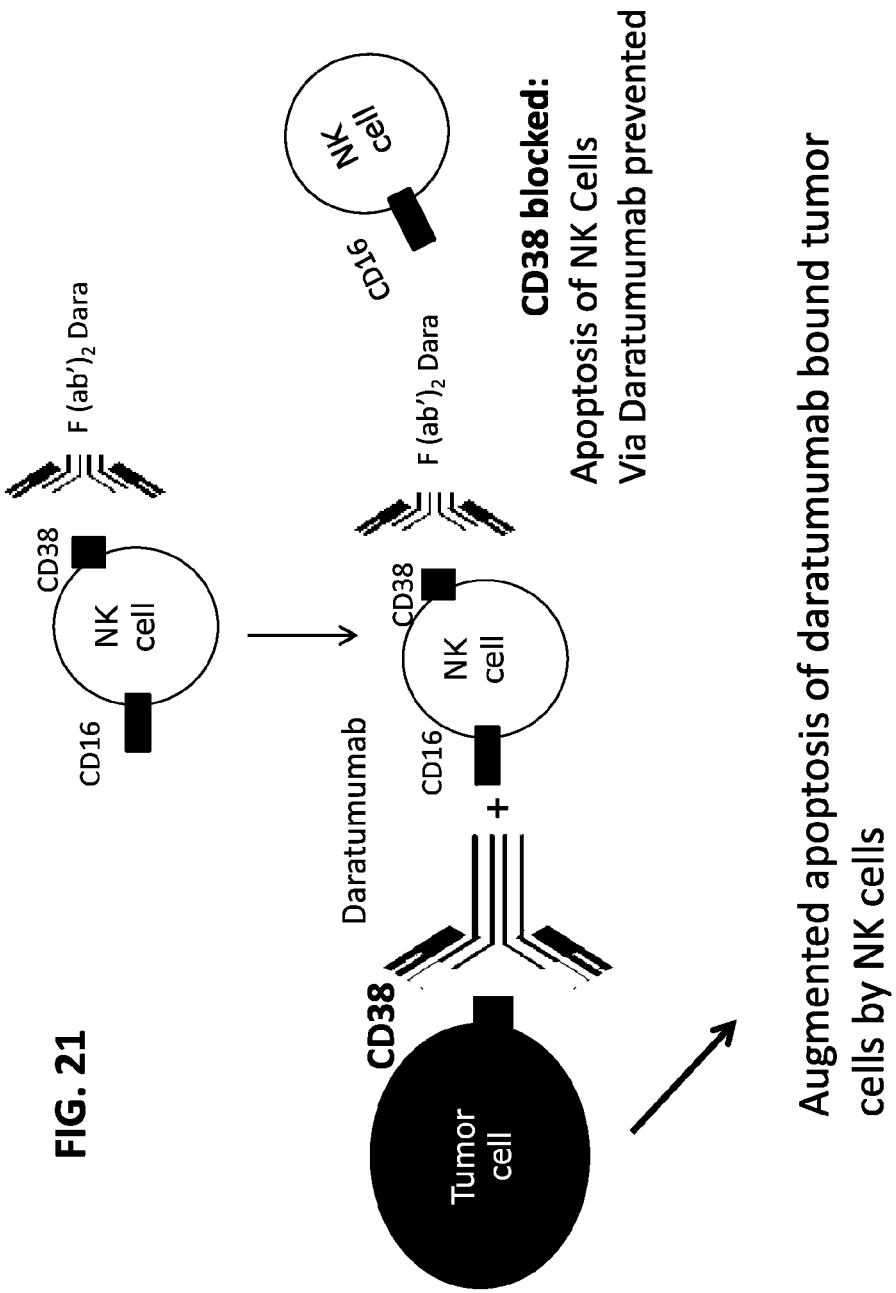

BLOCKING CD38 USING ANTI-CD38 F(AB')2 TO PROTECT NK CELLS

CROSS REFERENCE TO RELATED APPLICATION

This is the § 371 U.S. National Stage of International Application No. PCT/US2015/035832, filed Jun. 15, 2015, which was published in English under PCT Article 21(2), which in turn claims the benefit of U.S. Provisional Application No. 62/012,864, filed Jun. 16, 2014, which is incorporated herein by reference in its entirety.

FIELD

This disclosure relates to methods of protecting natural killer cells from anti-CD38 antibody-induced cell death using an anti-CD38 F(ab')$_2$ fragment, particularly methods of treating or inhibiting a hyperproliferative disorder in a subject.

BACKGROUND

Multiple myeloma (MM) is a malignancy of plasma cells, which are part of the B cell lineage. The median overall survival for patients with MM is about 4-7 years, and development of drug resistance is frequent. Immunotherapies for MM using anti-CD38 antibodies are in clinical trials and show promise. However, development of additional therapies for MM and other cancers expressing CD38 are still needed to improve patient survival and quality of life.

SUMMARY

It is identified herein that an anti-CD38 antibody causes cell death of natural killer (NK) cells by antibody-dependent cell-mediated cytotoxicity (ADCC) through a mechanism involving CD16. This is hypothesized to decrease the efficacy of treatment with an anti-CD38 antibody in a subject with a disorder (such as a hyperproliferative disorder), by presumably decreasing the number of NK cells available to kill the anti-CD38 antibody-bound target cells (such as tumor cells) by ADCC or other mechanisms. However, if the NK cells are contacted with a F(ab')$_2$ fragment of an anti-CD38 antibody prior to encountering an intact anti-CD38 antibody and the target cell, the NK cells are protected from anti-CD38 antibody-induced cell death and are available to kill the target cells. Thus, provided herein are methods of inhibiting growth or proliferation of cells expressing CD38 (such as tumor cells expressing CD38) by contacting the CD38-expressing cells with 1) NK cells bound to an anti-CD38 F(ab')$_2$ fragment and 2) an anti-CD38 antibody, in either order or simultaneously. Also provided herein are methods of treating or inhibiting a hyperproliferative disorder or an autoimmune disorder in a subject by administering to the subject 1) NK cells bound to an anti-CD38 F(ab')$_2$ fragment and 2) an anti-CD38 antibody, in either order or simultaneously.

In some embodiments, disclosed herein are methods for inhibiting growth or proliferation of cells expressing CD38 (such as tumor cells or autoimmune disorder-associated cells expressing CD38). The methods can include contacting a population of NK cells with a F(ab')$_2$ fragment of a first anti-CD38 antibody to produce a population of NK cells bound to the F(ab')$_2$ fragment of the first anti-CD38 antibody and contacting the CD38-expressing cells with 1) the population of NK cells bound to the F(ab')$_2$ fragment of the first anti-CD38 antibody and 2) a second anti-CD38 antibody or a fragment thereof in either order or simultaneously. In one non-limiting example, the F(ab')$_2$ fragment of the first anti-CD38 antibody is a F(ab')$_2$ fragment of daratumumab and the second anti-CD38 antibody is intact daratumumab.

In other embodiments, disclosed herein are methods for treating or inhibiting a hyperproliferative disorder (including, but not limited to multiple myeloma) or an autoimmune disorder by administering to a subject having a hyperproliferative disorder or an autoimmune disorder 1) a population of NK cells bound to a F(ab')$_2$ fragment of a first anti-CD38 antibody and 2) a second anti-CD38 antibody (in either order or simultaneously). In one non-limiting example, the F(ab')$_2$ fragment of the first anti-CD38 antibody is a F(ab')$_2$ fragment of daratumumab and the second anti-CD38 antibody is intact daratumumab.

Also disclosed herein are pharmaceutical compositions that include a population of NK cells bound to a F(ab')$_2$ fragment of an anti-CD38 antibody and a pharmaceutically acceptable carrier. The pharmaceutical composition can be used to treat a subject having a hyperproliferative disorder or to decrease growth or proliferation of cells expressing CD38, for example utilizing the methods disclosed herein.

The foregoing and other features of the disclosure will become more apparent from the following detailed description, which proceeds with reference to the accompanying figures.

BRIEF DESCRIPTION OF THE DRAWINGS

FIG. 1 is a plot showing expression of CD38 on T cells, NK cells, B cells, and myeloma cells.

FIG. 2A is a flow cytometry plot and FIG. 2B is a bar graph showing CD38 expression in fresh NK cells, NK cells treated with IL-2 for 18 hours, and NK cells expanded for 7 days in IL-2 containing media on EBV-LCL feeder cells.

FIGS. 4A and 4B are a series of panels showing CD16 and CD38 expression in expanded NK cells. FIG. 4A shows CD16$^+$ NK cells and FIG. 4B shows CD16$^-$ NK cells.

FIG. 6A shows K562 tumor cells; FIG. 6B shows MM1S tumor cells; FIG. 6C shows OPM1 tumor cells.

FIGS. 7A-7C are a series of graphs showing % lysis of tumor cells when daratumumab is added to the tumor cells at 1 µg/ml or 10 µg/ml then washed off, followed by four hour co-culture with NK cells. Control represents no daratumumab added to the tumor cells. FIG. 7A shows K562 tumor cells; FIG. 7B shows MM1S tumor cells; FIG. 7C shows OPM1 tumor cells.

FIGS. 8A and 8B are a series of panels showing expression of CD38 in NK cells from two donors with low affinity CD16 genotype. Left panels show CD38 staining on NK cells from both donors and right panels show CD38 staining on NK cells from both donors when NK cells have been pretreated with daratumumab at 10 μg/ml. FIG. 8A shows donor 1 (D64) and FIG. 8B shows Donor 2 (D136).

FIGS. 9A and 9B are a series of panels showing expression of CD38 in NK cells from two donors with high affinity CD16 genotype. Left panels show CD38 expression on NK cells from both donors and right panels show CD38 expression on NK cells from both donors when NK cells have been pretreated with daratumumab at 10 μg/ml. FIG. 9A shows donor 3 (D09) and FIG. 9B shows Donor 4 (D96).

FIGS. 10A and 10B are a series of panels showing the effect of daratumumab on CD16⁻ (FIG. 10A) or CD16⁺ (FIG. 10B) NK cell viability in high affinity CD16 genotype NK cells (D96) with or without (control) daratumumab treatment.

FIGS. 11A and 11B are graphs showing U226 myeloma cell lysis by low affinity CD16 NK cells (FIG. 11A) or high affinity CD16 NK cells (FIG. 11B) when tumor cells are cultured with daratumumab alone, NK cells alone, or NK cells and daratumumab.

FIGS. 18A-18C are a series of panels showing the effect of intact daratumumab on F(ab')$_2$ pre-treated NK cells. NK cells were treated daratumumab (FIG. 18A), F(ab')$_2$ of atumumab (FIG. 18B), or daratumumab F(ab')$_2$ (FIG. 18C), then cultured with intact daratumumab four days later. Viable NK cells (left lower quadrant of each panel) were greatest among F(ab')$_2$ pre-treated NK cells.

FIG. 21 is a schematic showing a proposed mechanism for protecting NK cells from daratumumab-induced cell death using daratumumab F(ab')$_2$ fragment. NK cell CD38 is bound to daratumumab F(ab')$_2$, blocking daratumumab-induced killing of NK cells by antibody-dependent cell-mediated cytotoxicity (ADCC). If tumor cells expressing CD38 are contacted with intact daratumumab and the NK cells to which the daratumumab F(ab')$_2$ is bound, killing of the tumor cells is augmented because the NK cell population is protected.

DETAILED DESCRIPTION

I. Abbreviations

Figure 2A:
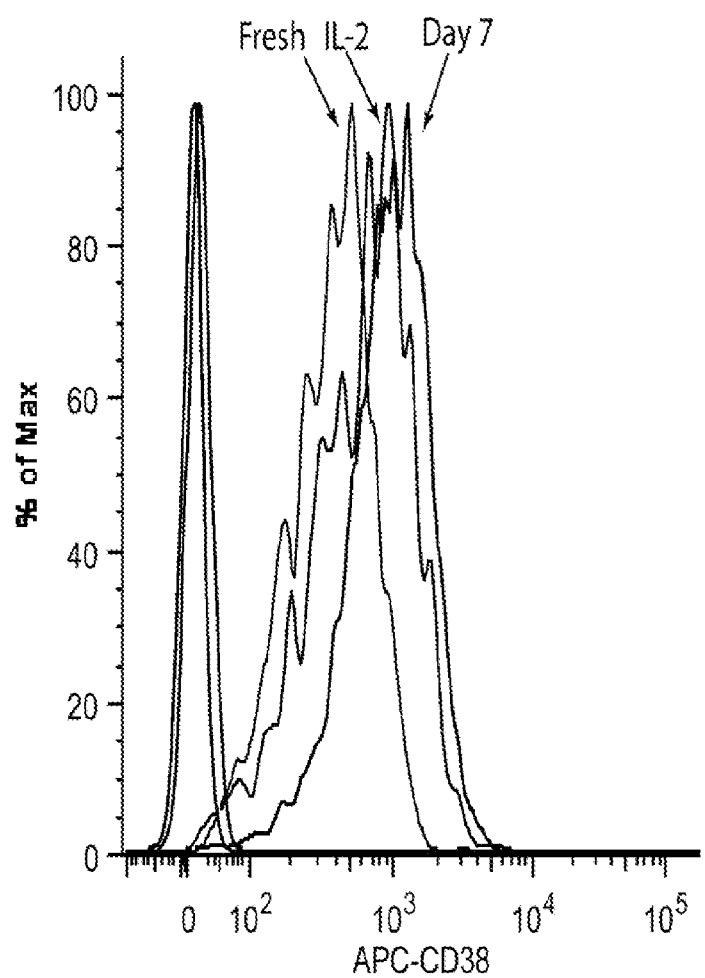
FIGS. 2A and 2B are graphs showing the effect of activation and expansion on CD38 expression on NK cells.

ADCC antibody-dependent cell-mediated cytotoxicity
CDC complement-dependent cytotoxicity
F(ab')$_2$ dimer of an antigen-binding fragment of an antibody
i.p. intraperitoneally
i.v. intravenously
MM multiple myeloma
NK cells natural killer cells

II. Terms

Unless otherwise noted, technical terms are used according to conventional usage. Definitions of common terms in molecular biology may be found in Benjamin Lewin, *Genes VII*, published by Oxford University Press, 2000 (ISBN 019879276X); Kendrew et al. (eds.), *The Encyclopedia of Molecular Biology*, published by Blackwell Publishers, 1994 (ISBN 0632021829); Robert A. Meyers (ed.), *Molecular Biology and Biotechnology: a Comprehensive Desk Reference*, published by Wiley, John & Sons, Inc., 1995 (ISBN 0471186341); and George P. Rédei, *Encyclopedic Dictionary of Genetics, Genomics, and Proteomics*, 2nd Edition, 2003 (ISBN: 0-471-26821-6).

The following explanations of terms and methods are provided to better describe the present disclosure and to guide those of ordinary skill in the art to practice the present disclosure. The singular forms "a," "an," and "the" refer to one or more than one, unless the context clearly dictates otherwise. For example, the term "comprising a polypeptide" includes single or plural polypeptides and is considered equivalent to the phrase "comprising at least one polypeptide." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements.

All publications, patent applications, patents, and other references mentioned herein are incorporated by reference in their entirety for all purposes. All sequences associated with the GenBank Accession Nos. mentioned herein are incorporated by reference in their entirety as were present on Jun. 16, 2014, to the extent permissible by applicable rules and/or law. In case of conflict, the present specification, including explanations of terms, will control.

Although methods and materials similar or equivalent to those described herein can be used to practice or test the disclosed technology, suitable methods and materials are described below. The materials, methods, and examples are illustrative only and not intended to be limiting.

To facilitate review of the various embodiments of this disclosure, the following explanations of specific terms are provided:

Antibody: A protein (or protein complex) that includes one or more polypeptides substantially encoded by immunoglobulin genes or fragments of immunoglobulin genes. The recognized immunoglobulin genes include the kappa, lambda, alpha, gamma, delta, epsilon, and mu constant region genes, as well as the myriad of immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The basic immunoglobulin (antibody) structural unit is generally a tetramer. Each tetramer is composed of two identical pairs of polypeptide chains, each pair having one "light" (about 25 kDa) and one "heavy" (about 50-70 kDa) chain. The N-terminus of each chain defines a variable region of about 100 to 110 or more amino acids primarily responsible for antigen recognition. The terms "variable light chain" ($V_L$) and "variable heavy chain" ($V_H$) refer, respectively, to these light and heavy chains.

As used herein, the term "antibodies" includes intact immunoglobulins as well as a number of well-characterized fragments. For instance, Fabs, Fvs, and single-chain Fvs (scFvs) that bind to target protein (or epitope within a protein or fusion protein) would also be specific binding agents for that protein (or epitope). These antibody fragments are defined as follows: (1) Fab, the fragment which contains a monovalent antigen-binding fragment of an antibody molecule produced by digestion of whole antibody with the enzyme papain to yield an intact light chain and a portion of one heavy chain; (2) Fab', the fragment of an antibody molecule obtained by treating whole antibody with pepsin, followed by reduction, to yield an intact light chain and a portion of the heavy chain; two Fab' fragments are obtained per antibody molecule; (3) (Fab')$_2$, the fragment of the antibody obtained by treating whole antibody with the enzyme pepsin without subsequent reduction; (4) F(ab')$_2$, a dimer of two Fab' fragments held together by two disulfide bonds; (5) Fv, a genetically engineered fragment containing the variable region of the light chain and the variable region of the heavy chain expressed as two chains; and (6) single chain antibody, a genetically engineered molecule containing the variable region of the light chain, the variable region of the heavy chain, linked by a suitable polypeptide linker as a genetically fused single chain molecule. Methods of making these fragments are routine (see, for example, Harlow and Lane, *Using Antibodies: A Laboratory Manual*, CSHL, New York, 1999).

Binding/stable binding: An association between two substances or molecules, such as the association of an antibody or an antibody fragment (such as an F(ab')$_2$ fragment) with a polypeptide. An antibody binds or stably binds a target protein (e.g., CD38) when a sufficient amount of the antibody or antibody fragment binds to its target protein to permit detection of that binding. Binding can be detected by any procedure known to one skilled in the art, such as by physical or functional properties of the target:antibody complex. Physical methods of detecting the binding of a target protein to an antibody or antibody fragment, include but are not limited to, such methods as Western blotting, immunohistochemistry, flow cytometry, or other methods known to one of skill in the art.

CD16: Also known as Fc fragment of IgG, low affinity IIIa, receptor (FcγRIIIA) CD16 is a receptor for the Fc portion of immunoglobulin G, which is involved in antibody-dependent responses, and also removing antigen-antibody complexes from the circulation. CD16 is expressed on most NK cells as a transmembrane glycoprotein. About 90% of NK cells express CD16, while about 10% do not express CD16 or express low amounts of CD16. Exemplary human CD16 sequences include GenBank Accession Nos. NM_001127596, NM_001127595, NM_001127593, NM_001127592, and NM_000569 (nucleic acid sequences) and NP_001121068, NP_001121067, NP_001121065, NP_001121064, and NP_000560 (amino acid sequences), all of which are incorporated herein by reference as present in GenBank on Jun. 16, 2014.

A CD16 positive (CD16$^+$) cell (also referred to herein as a CD16-expressing cell) is a cell that expresses a detectable amount of CD16 protein (for example, using flow cytometry).

CD38: Also known as T10 or ADPRC1. The CD38 molecule is a type II transmembrane glycoprotein with a molecular weight of approximately 45 kD. It is a bifunctional ectoenzyme, capable of catalyzing conversion of nicotinamide adenine dinucleotide (NAD+) to cyclic ADP-ribose (cADPR) and conversion of cADPR into ADP-ribose. CD38 is also involved in cell adhesion and cellular signaling, including calcium mobilization. Exemplary human CD38 sequences include GenBank Accession Nos. NM_001775 (nucleic acid sequence) and NP_001766 (amino acid sequence), both of which are incorporated herein by reference as present in GenBank on Jun. 16, 2014.

A CD38 positive (CD38+) cell (also referred to herein as a CD38-expressing cell) is a cell that expresses a detectable amount of CD38 protein (for example, using flow cytometry). In some examples, a cell expressing an increased amount of CD38 compared to a control sample or reference value is referred to as over-expressing CD38.

Contacting: Placement in direct physical association, including both a solid and liquid form. Contacting can occur in vitro or ex vivo with isolated cells or tissue or in vivo by administering to a subject.

Daratumumab: A human CD38 monoclonal antibody (also known as HUMAX®-CD38). See, e.g., de Weers et al., *J. Immunol.* 186:1840-1848, 2011; U.S. Pat. No. 7,829,673. Daratumumab exhibits cytotoxic activity through several mechanisms, including ADCC, CDC, and apoptosis. In ongoing clinical trials, daratumumab has exhibited positive effects against multiple myeloma.

Effective amount: An amount of a preparation that alone, or together with a pharmaceutically acceptable carrier or one or more additional agents, induces the desired response. A therapeutic agent or preparation, such as an antibody or antibody fragment, or a preparation of cells bound to an antibody or antibody fragment, is administered in therapeutically effective amounts. Effective amounts a therapeutic agent can be determined in many different ways, such as assaying for a reduction in symptoms or improvement of physiological condition of a subject having a disorder (such as a hyperproliferative disorder). Effective amounts also can be determined through various in vitro, in vivo, or in situ assays.

Hyperproliferative disorder: Any of a number of diseases that are characterized by uncontrolled, abnormal proliferation of cells, the ability of affected cells to spread locally or through the bloodstream and lymphatic system to other parts of the body (for example, metastasize), and/or any of a number of characteristic structural or molecular features. In some examples, a hyperproliferative disorder includes a tumor (such as a benign or malignant tumor) or a hematological malignancy (such as a leukemia or lymphoma).

Isolated: An "isolated" biological component (such as a nucleic acid molecule, protein, or cell) has been substantially separated or purified away from other biological components in a preparation, cell, or organism in which the component occurs, such as other chromosomal and extrachromosomal DNA and RNA, proteins and cells. Proteins (such as antibodies or antibody fragments) that have been "isolated" include proteins purified by standard purification methods. The term also embraces proteins prepared by recombinant expression in a host cell as well as chemically synthesized proteins. An isolated cell can be an NK cell that is substantially separated from other cell subtypes.

Natural killer (NK) cells: A form of lymphocyte that is a component of the innate immune system. NK cells are cytotoxic to target cells, including tumor cells and virally infected cells. In some examples, NK cells recognize cells with surface-bound antibodies via CD16 (FyRIII), resulting in activation of the NK cells and release of cytolytic granules, leading to apoptosis of the target cell.

NK cells are $CD3^-/CD56^+$ cells that typically make up about 5-15% of circulating lymphocytes. They are further divided into two sub-populations based on the level of CD56 expression and whether they are positive or negative for CD16 (e.g., $CD56^{dim}CD16^+$ and $CD56^{bright}CD16^-$). The $CD16^+$ sub-population makes up about 90% of the total NK cell population.

Pharmaceutically acceptable carrier: The pharmaceutically acceptable carriers (vehicles) useful in this disclosure are conventional. *Remington: The Science and Practice of Pharmacy*, The University of the Sciences in Philadelphia, Editor, Lippincott, Williams, & Wilkins, Philadelphia, Pa., 21$^{st}$ Edition (2005), describes compositions and formulations suitable for pharmaceutical delivery of one or more therapeutic compositions. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Purified: The term "purified" does not require absolute purity; rather, it is intended as a relative term. Thus, for example, a purified protein preparation is one in which the protein referred to is more pure than the protein in its environment (such as within a cell). For example, a preparation of a protein is purified such that the protein represents at least 50% (for example, at least 70%, 80%, 90%, 95%, 98%, or more) of the total protein content of the preparation. Similarly a purified population of cells is one in which the cells referred to (such as NK cells) is more pure than the cells in their natural environment in an organism, for example, the cell type represents at least 50% (for example, at least 70%, 80%, 90%, 95%, 98%, or more) of the total cell content of the preparation.

Subject: Living multi-cellular vertebrate organisms, a category that includes human and non-human mammals.

Treating or inhibiting: "Treating" a disease or disorder refers to a therapeutic intervention that ameliorates a sign or symptom of a disease or pathological condition (such as a hyperproliferative disorder) after it has begun to develop. "Inhibiting" a disease refers to inhibiting the full development of a disease. Inhibition of a disease can span the spectrum from partial inhibition to substantially complete inhibition (e.g., including, but not limited to prevention) of the disease. In some examples, the term "inhibiting" refers to reducing or delaying the onset or progression of a disease. A subject to be treated, such as with the methods disclosed herein, can be identified by standard diagnosing techniques for such a disorder, for example, symptoms, family history, or risk factors to develop the disease or disorder.

Tumor: A neoplasm that may be either malignant or non-malignant (benign). Tumors of the same tissue type are tumors originating in a particular organ (such as brain, breast, lung, or colon) or cell type (such as glial cell, for example astrocyte or oligodendrocyte). Tumors include original (primary) tumors, recurrent tumors, and metastases (secondary tumors). A tumor recurrence is the return of a tumor, at the same site (for example, in the same organ or tissue) as the original (primary) tumor, after the tumor has been removed surgically, by drug or other treatment, or has otherwise disappeared. A metastasis is the spread of a tumor from one part of the body to another. Tumors formed from cells that have spread are called secondary tumors (or metastatic tumors) and contain cells that are like those in the original (primary) tumor. There can be a recurrence of either a primary tumor or a metastasis.

III. Overview of Several Embodiments

Disclosed herein are methods of inhibiting or protecting NK cells from anti-CD38 antibody-induced cell death. Thus, provided herein are methods of inhibiting growth or proliferation of cells expressing CD38 (such as tumor cells or autoimmune cells expressing CD38) by contacting the CD38-expressing cells with 1) NK cells bound to an anti-CD38 F(ab')$_2$ fragment and 2) an anti-CD38 antibody. Also provided herein are methods of treating or inhibiting a hyperproliferative disorder or an autoimmune disorder in a subject by administering to the subject 1) NK cells bound to an anti-CD38 F(ab')$_2$ fragment and 2) an anti-CD38 antibody.

A. Methods of Inhibiting Growth or Proliferation of CD38-Expressing Cells

In some embodiments, the methods provided herein inhibit growth or proliferation of CD38-expressing cells (for example solid tumor or hematological malignancy cells that express CD38). The methods can include contacting a population of NK cells (for example $CD16^+$ NK cells) with a F(ab')$_2$ fragment of a first anti-CD38 antibody for a period of time sufficient to produce a population of NK cells bound to the F(ab')$_2$ fragment (for example for about 10 minutes to about 2 hours). In some examples, the NK cells are contacted with about 0.1 µg/ml to 50 µg/ml (such as about 0.5-10 µg/ml, about 1-25 µg/ml, about 10-50 µg/ml, for example, about 1 µg/ml, about 2.5 µg/ml, about 5 µg/ml, about 10 µg/ml, about 25 µg/ml, or more) of the F(ab')$_2$ fragment of the first anti-CD38 antibody. In particular examples, the NK cells are contacted with the anti-CD38 F(ab')$_2$ fragment in vitro or ex vivo, for example, following isolation of NK cells from a sample from a subject. The NK cells may be expanded prior to contacting the population of NK cells with the F(ab')$_2$ fragment of the first anti-CD38 antibody. NK cells, their optional expansion, and contacting a population of NK cells with a F(ab')$_2$ fragment to produce a population of NK cells bound to the F(ab')$_2$ fragment are described in greater detail in Section V, below.

The population of NK cells bound to the first anti-CD38 antibody F(ab')$_2$ fragment are then contacted with one or more cells expressing CD38 (such as a population of cells, for example a population of tumor cells expressing CD38) and a second anti-CD38 antibody. In some examples, the CD38-expressing cells are contacted with about 0.01 µg/ml to about 1 mg/ml (such as about 0.1-1 µg/ml, about 0.5-10 µg/ml, about 1-251.1 g/ml, about 5-50 µg/ml, about 10-100 µg/ml, about 25-500 µg/ml, for example, about 0.05 µg/ml, about 1 µg/ml, about 5 about 10 µg/ml, about 25 µg/ml, about 50 µg/ml, about 100 µg/ml, about 250 µg/ml, about 500 µg/ml, or more) of the second anti-CD38 antibody. The CD38-expressing cell (which in some examples is not a NK cell) is contacted with the population of NK cells bound to the F(ab')$_2$ fragment of the first anti-CD38 antibody and the second CD38 antibody sequentially, substantially simultaneously, or simultaneously. In one example, the CD38-expressing cell is contacted with the second anti-CD38 antibody prior to being contacted with the population of NK cells bound to the F(ab')$_2$ fragment of the first anti-CD38 antibody. In some examples, the CD38-expressing cell is contacted with the second anti-CD38 antibody for at least 1 hour to 48 hours (for example, about 2 hours, about 4 hours, about 8 hours, about 12 hours, about 18 hours, about 24 hours, or about 36 hours) before contacting the cells with the population of NK cells bound to the F(ab')$_2$ fragment of the first anti-CD38 antibody.

In some examples, the step of contacting the CD38-expressing cell(s) with the population of NK cells bound to the F(ab')$_2$ fragment of the first anti-CD38 antibody occurs in vitro or ex vivo. In other examples, the step of contacting the CD38-expressing cell(s) with the population of NK cells bound to the F(ab')$_2$ fragment of the first anti-CD38 antibody occurs in vivo, for example, by administering the population of NK cells bound to the F(ab')$_2$ fragment of the first anti-CD38 antibody to a subject (such as a subject with a hyperproliferative disorder). In such in vivo methods, the second anti-CD38 antibody is also administered to the subject, before, after, or substantially simultaneously with the population of NK cells bound to the F(ab')$_2$ fragment of the first anti-CD38 antibody. In one non-limiting example, the second anti-CD38 antibody is administered to the subject at least 1 hour to one week (for example, about 2 hours, about 12 hours, about 24 hours, about 48 hours, about 3 days, about 4 days, about 5 days, about 6 days, or about 7 days) before administering the population of NK cells bound to the F(ab')$_2$ fragment of the first anti-CD38 antibody. The population of NK cells may be autologous NK cells, for example, NK cells that have been isolated from the same subject and contacted with the F(ab')$_2$ fragment of the first anti-CD38 antibody ex vivo. These NK cells may be collected and bound by anti-CD38 F(ab')$_2$ fragments immediately after collection, following ex vivo activation with cytokines, or following ex vivo expansion/culturing before they are administered to the subject.

In some examples, the first and second anti-CD38 antibodies are the same antibody (that is the F(ab')$_2$ fragment is produced from the same antibody as the antibody contacted with the CD38-expressing cells). In other examples, the first anti-CD38 and the second anti-CD38 antibody are different. In particular example, the anti-CD38 antibodies are human antibodies. Anti-CD38 antibodies for use in the methods disclosed herein are discussed in Section IV below. In one non-limiting example, the first and second antibodies are daratumumab.

Methods of assessing the growth or proliferation of cells include determining cell number, for example before and after contacting the CD38-expressing cells with the population of NK cells bound to the F(ab')$_2$ fragment of the first anti-CD38 antibody and the second anti-CD38 antibody. A decrease (or no statistically significant increase) in the number of the CD38-expressing cells after treatment indicates that the growth or proliferation of the cells has been inhibited. Methods of determining cell number include counting the number of cells, for example by visualizing the cells, using a Coulter counter, or by flow cytometry. Growth or proliferation of cells can also be determined using cell viability assays (for example using fluorescent DNA binding dyes such as 7-aminoactinomycin D or tetrazolium reduction assays), or by determining the number of apoptotic or dead cells (for example, by flow cytometry (for example, detecting Annexin V), TUNEL assay, LDH assay, measuring intracellular caspases, or $^{51}$Cr release assay). A decrease (or no statistically significant increase) in the number of viable cells, or an increase in the number of apoptotic or dead cells after contacting the CD38-expressing cells with the population of NK cells bound to the F(ab')$_2$ fragment of the first anti-CD38 antibody and the second anti-CD38 antibody (for example compared to prior to the treatment) indicates that the growth or proliferation has been inhibited. If the population of NK cells bound to the F(ab')$_2$ fragment of the first anti-CD38 antibody and the second anti-CD38 antibody are administered to a subject, the number, viability, or amount of cell death can be determined in a sample from the subject (for example in a tumor sample or a blood sample from the subject), by imaging studies (such as CT scan, PET/CT scan, MRI, skeletal series, or bone scan), or by assessment of tumor size by physical examination.

B. Methods of Treating or Inhibiting a Hyperproliferative Disorder

In some embodiments, the methods provided herein treat or inhibit a hyperproliferative disorder in a subject (for example a subject with a solid tumor or hematological malignancy cells). The methods include administering to the subject 1) an effective amount (such as a therapeutically effective amount) of a population of NK cells bound to a F(ab')$_2$ fragment of a first anti-CD38 antibody and 2) administering to the subject an effective amount (such as a therapeutically effective amount) of a second anti-CD38 antibody. The second anti-CD38 antibody is administered to the subject before, after, or substantially simultaneously with the population of NK cells bound to the F(ab')$_2$ fragment of the first anti-CD38 antibody. In some examples, the subject is administered the second anti-CD38 antibody at least about 1 hour to 3 weeks (for example, about 2 hours, about 12 hours, about 24 hours, about 48 hours, about 3 days, about 4 days, about 5 days, about 6 days, about 7 days, about 10 days, about 14 days, or about 21 days) before administration of the population of NK cells bound to the F(ab')$_2$ fragment of the first anti-CD38 antibody. In particular examples, the subject has a solid tumor or hematological malignancy that expresses CD38. Dosing, routes of administration and timing of administration are described in further detail in Section VI, below.

The population of NK cells bound to the F(ab')$_2$ fragment of a first anti-CD38 antibody is produced by contacting NK cells (for example CD16$^+$ NK cells) with a F(ab')$_2$ fragment of the first anti-CD38 antibody for a period of time sufficient to produce a population of NK cells bound to the F(ab')$_2$ fragment (for example for about 10 minutes to about 2 hours). In particular examples, the NK cells are contacted with the anti-CD38 F(ab')$_2$ fragment in vitro or ex vivo, for example, following isolation of NK cells from a sample from a subject. The NK cells may be collected and bound by anti-CD38 F(ab')$_2$ fragments immediately after collection, following ex vivo activation with cytokines, or following ex vivo expansion/culturing. The population of NK cells may be autologous NK cells, for example, NK cells that have been isolated from the same subject and contacted with the F(ab')$_2$ fragment of the first anti-CD38 antibody ex vivo. Alternatively, the NK cells may be allogeneic. Allogeneic NK cells may be from a related or unrelated donor and may be either partially or fully HLA-matched. NK cells, their optional ex vivo activation or expansion, and contacting a population of NK cells with a F(ab')$_2$ fragment to produce a population of NK cells bound to the F(ab')$_2$ fragment are described in greater detail in Section V, below.

In some examples, the first and second anti-CD38 antibodies are the same antibody (that is the F(ab')$_2$ fragment is produced from the same antibody as the antibody contacted with the CD38-expressing cells). In other examples, the first anti-CD38 and the second anti-CD38 antibody are different. In particular example, the anti-CD38 antibodies are human antibodies. Anti-CD38 antibodies for use in the methods disclosed herein are discussed in Section IV below. In one non-limiting example, the first and second antibodies are daratumumab.

C. Pharmaceutical Compositions

Also disclosed herein are pharmaceutical compositions comprising a population of NK cells bound to a F(ab')$_2$ fragment of an anti-CD38 antibody and a pharmaceutically acceptable carrier. In some examples, the F(ab')$_2$ fragment is from a human, humanized, or chimeric anti-CD38 antibody. In one non-limiting example, the F(ab')$_2$ fragment is from daratumumab; however, the F(ab')$_2$ fragment of any anti-CD38 antibody can be used. In some examples, the composition includes about $10^4$ to $10^{11}$ NK cells bound to a F(ab')$_2$ fragment of an anti-CD38 antibody. For example, the composition may be prepared such that about $10^6$ to $10^9$ NK cells/kg are administered to a subject.

In some examples, the compositions include pharmaceutically acceptable carriers and/or one or more additional agents. Actual methods for preparing administrable compositions will be known or apparent to those skilled in the art and are described in more detail in such publications as *Remington: The Science and Practice of Pharmacy*, The University of the Sciences in Philadelphia, Editor, Lippincott, Williams, & Wilkins, Philadelphia, Pa., 21$^{st}$ Edition (2005).

The composition may be prepared by contacting a population of NK cells with an anti-CD38 antibody F(ab')$_2$ fragment for a period of time sufficient to produce a population of NK cells bound to the F(ab')$_2$ fragment (for example, as described in Section V). The NK cells bound to the F(ab')$_2$ fragment may be washed (for example, to remove culture medium (if present), unbound F(ab')$_2$ fragments, or other components). The NK cells are then resuspended in a pharmaceutically acceptable carrier, which may include additional preservatives, surfactants, or other therapeutic agents. In some examples, the composition is stored (for example, at –20° C. or –80° C.) until use. In other examples, NK cells are frozen after collection and optional ex vivo activation or expansion, and are later thawed and contacted with an anti-CD38 antibody F(ab')$_2$ fragment prior to administration to a subject.

IV. Anti-CD38 Antibodies

The CD38 molecule is a type II transmembrane glycoprotein with a molecular weight of approximately 45 kD. It is a bifunctional ectoenzyme, capable of catalyzing conversion of nicotinamide adenine dinucleotide (NAD$^+$) to cyclic ADP-ribose (cADPR) and conversion of cADPR into ADP-ribose. CD38 is also involved in cell adhesion and cellular signaling, including calcium mobilization. CD38 is expressed by hematopoietic cells, including medullary thymocytes, activated T and B cells, NK cells, monocytes, lymph node germinal center lymphoblasts, plasma B cells, and it can also be expressed by dendritic cells. Many normal bone marrow cells, including precursor cells, also express CD38. In addition to hematopoietic cells, CD38 is also expressed on intra-epithelial cells and lamina propria cells in the gut, Purkinje cells, pancreatic β-cells, prostate epithelial cells, osteoclasts, retinal cells, and muscle. Exemplary human CD38 sequences include GenBank Accession Nos. NM_001775 (nucleic acid sequence) and NP_001766 (amino acid sequence), both of which are incorporated herein by reference as present in GenBank on Jun. 16, 2014.

CD38 expression is up-regulated in hematological malignancies, including but not limited to multiple myeloma, chronic lymphocytic leukemia, acute lymphocytic leukemia, acute myeloid leukemia, chronic myeloid leukemia, pro-lymphocytic/myelocytic leukemia, plasma cell leukemia, NK cell leukemia, Waldenstrom macroglobulinemia, Hodgkin's lymphoma, non-Hodgkin's lymphoma, mantle cell lymphoma, diffuse large B-cell lymphoma, and follicular lymphoma. Increased expression of CD38 may also occur in solid tumors, including but not limited to colorectal tumors, lung carcinoma, prostate cancer, pancreatic cancer (for example, insulinoma), breast cancer, neuroblastoma, testicular cancer (such as seminoma), and ovarian cancer.

Certain anti-CD38 monoclonal antibodies can affect the viability and growth of tumor cells. These antibodies have been shown to mediate killing of CD38$^+$ tumor cells by CDC, ADCC, and/or apoptosis. Two anti-CD38 monoclonal antibodies, daratumumab and SAR650984, are currently in clinical trials for treatment of multiple myeloma and have shown promising results.

In some examples, the presently disclosed methods utilize antibodies or antigen binding fragments thereof (such as F(ab')$_2$ fragments) that specifically or stably bind CD38. In some embodiments, the antibody is a monoclonal antibody. The antibody can be a fully human, humanized or a chimeric antibody. However, other antibody forms, such as camelids can be used in the methods disclosed herein. Generally, these antibodies specifically or stably bind CD38. In particular examples, the antibodies used in the methods disclosed herein are human antibodies.

Antibodies that specifically or stably bind CD38 are commercially available and are known in the art. For example, antibodies that bind human CD38 are disclosed in U.S. Pat. Nos. 7,829,673; 8,153,765; and 8,263,746; each of which are incorporated herein by reference in their entirety. Such antibodies include antibodies (and antigen binding fragments derived from the antibodies) known as daratumumab (also known as HuMax®-CD38; Genmab, Princeton, N.J.; de Weers et al., *J. Immunol.* 186:1840-1848, 2011; U.S. Pat. No. 7,829,673) and SAR650984 (Sanofi, Bridgewater, N.J.; U.S. Pat. No. 8,153,765; 2011/0262454). Additional antibodies that bind CD38 include for example, OKT10 (Stevenson et al., *Blood* 77:1071-1079, 1991), AT13/5 (U.S. Pat. App. Publ. No. 2002/0164788), IB4 (Zupo et al., *Eur. J. Immunol.* 24:12180111, 1994; Morra et al., *FASEB J.* 12:581-592, 1998), T16 (Kumagai et al., *J. Exp. Med.* 1101-1110, 1995; Todisco et al., *Blood* 95:535-542, 2000), and antibodies described in WO 2005/103083. At least some of these antibodies mediate killing of CD38$^+$ cells by CDC, ADCC, and/or apoptosis.

In certain embodiments, the disclosed methods utilize a F(ab')$_2$ fragment of an anti-CD38 antibody. F(ab')$_2$ fragments are produced by pepsin digestion of whole IgG antibodies, which removes most of the Fc region, but leaves intact some of the hinge region. F(ab')$_2$ fragments have two antigen-binding F(ab) portions that are linked together by disulfide bonds. Methods of producing F(ab')$_2$ antibody fragments are known to one of skill in the art and kits for F(ab')$_2$ fragment production are commercially available, such as Pierce F(ab')$_2$ Preparation Kit (Thermo-Scientific Pierce, Rockford, Ill.) or F(ab')$_2$ Fragmentation Kit (G-Biosciences, St. Louis, Mo.). In some examples, the F(ab')$_2$ fragments are purified, for example using Protein A to remove the digested Fc portion from the F(ab')$_2$ fragments. In other examples, undigested intact antibody is also removed from the F(ab')$_2$ fragment preparation. The F(ab')$_2$ fragments can be purified away from any undigested antibody and the non-F(ab')$_2$ components of the antibody (e.g., the Fc component) using a protein A/G column. The purity of the F(ab')$_2$ fragments can be assessed, for example, using gel electrophoresis.

In one non-limiting example, the antibody that specifically binds CD38 is daratumumab. Daratumumab is a human monoclonal antibody that specifically binds CD38 (e.g., U.S. Pat. No. 7,829,673). Daratumumab binds to an epitope on human CD38 that includes amino acids 233-246 and 267-280, of which serine 274 has been identified as particularly important for antibody binding (de Weers et al., *J. Immunol.* 186:1840-188, 2011). In some embodiments, the methods disclosed herein utilize a F(ab')$_2$ fragment of daratumumab (for example, for pre-treatment of NK cells). In other embodiments, the methods disclosed herein utilize intact daratumumab (for example, for administration to a subject alone or in conjunction with NK cells pre-treated with a F(ab')$_2$ fragment of an anti-CD38 antibody). In still further embodiments, the methods utilize both F(ab')$_2$ fragments of daratumumab and intact daratumumab.

V. NK Cell Expansion and Pre-Treatment

NK cells are non-T, non-B lymphocytes with intracellular granules that are a component of the innate immune system. They are the effectors in ADCC that can kill sensitive targets, including tumor cells and virally infected cells. ADCC is triggered when receptors on the NK cell surface (such as CD16) recognize IgG1 or IgG3 antibodies bound to the surface of a cell. This triggers release of cytoplasmic granules containing perforin and granzymes, leading to cell death.

NK cells are CD3$^-$/CD56$^+$ cells that typically make up about 5-15% of circulating lymphocytes. They are further divided into two sub-populations based on the level of CD56 expression and whether they are positive or negative for CD16 (e.g., CD56$^{dim}$CD16$^+$ and CD56$^{bright}$CD16$^-$). The CD16$^+$ sub-population makes up about 90% of the total NK cell population.

In the methods disclosed herein, a population of NK cells is contacted with a F(ab')$_2$ fragment of an anti-CD38 antibody to produce a population of NK cells bound to the F(ab')$_2$ fragment. In some examples, the population of NK cells is an isolated or purified population of NK cells, such as a preparation that is at least 70% (such as at least 80%, 90%, 95%, 98%, 99%, or more) NK cells, for example a preparation that is substantially free of cells other than NK cells. In some examples, the NK cell population is substantially free of B cells and/or T cells. A population of NK cells for use in the disclosed methods can be obtained by any means known to one of skill in the art or developed in the future. The NK cells may be collected and bound by anti-CD38 F(ab')$_2$ fragments immediately after collection, following ex vivo activation with cytokines, or following ex vivo expansion/culturing. In some examples, the NK cells are cultured ex vivo for up to 42 days following collection.

In particular examples, NK cells are isolated from a blood sample by depleting the sample of CD3$^+$ cells. In some examples, following CD3$^+$ depletion, the remaining cells are selected for CD56$^+$ cells and/or depleted of CD19$^+$ cells. In other examples, NK cells are isolated by a negative NK cell depletion method, for example which depletes the sample of CD3$^+$ T-cells and other non-NK cell populations such as B cells and myeloid cells. In some examples, the sample is also selected for CD16$^+$ cells, to produce a population of CD16$^+$ NK cells. The NK cell population can be selected for the presence or absence of particular cell surface markers such as CD3, CD56, CD19 and/or CD16 by methods known to one of skill in the art, for example using flow cytometry techniques.

The population of NK cells is contacted with a F(ab')$_2$ fragment of an anti-CD38 antibody (such as a F(ab')$_2$ fragment of the first anti-CD38 antibody, for example daratumumab) in vitro or ex vivo. The amount of F(ab')$_2$ fragment used is an amount sufficient to produce stable binding to CD38 present on the NK cells. In some examples, the amount of F(ab')$_2$ fragment added is an amount sufficient to bind at least 50% (for example, at least 60%, 70%, 75%, 80%, 90%, 95%, or even 100%) of the CD38 epitopes present on the NK cells. In other examples, if the intact anti-CD38 antibody were to be subsequently added to these NK cells it would not be able to substantially bind CD38 present on the NK cell surface, as the CD38 epitopes would be bound by the F(ab')$_2$ fragments. In some examples, the population of NK cells is contacted with about 0.1 µg/ml to about 100 µg/ml (such as about 0.5-10 µg/ml, about 1-25 µg/ml, about 10-50 µg/ml, about 25-100 µg/ml, for example, about 1 µg/ml, about 2.5 µg/ml, about 5 µg/ml, about 10 µg/ml, about 25 µg/ml, about 50 µg/ml, about 75 µg/ml or more) of the F(ab')$_2$ fragment. The NK cells are contacted with the F(ab')$_2$ fragment for a period of time sufficient to produce stable binding of the F(ab')$_2$ fragment to the NK cells, for example at least about 5 minutes to 4 hours (such as about 10 minutes, about 15 minutes, about 20 minutes, about 30 minutes, about 1 hour, about 2 hours, about 3 hours, or about 4 hours). The NK cells are contacted with the F(ab')$_2$ fragment in a suitable medium, such as a suitable NK cell culture medium (for example X-VIVO™ medium; Lonza, Basel, Switzerland) and at a temperature sufficient for binding of the F(ab')$_2$ fragment to CD38, for example at 4° C. to 37° C., such as at room temperature in some examples.

It has been identified herein that the F(ab')$_2$ fragment of an anti-CD38 antibody can stably bind to NK cells for a period of time following removal of the F(ab')$_2$ fragment from the medium (for example, following washing of the NK cells after contacting with the F(ab')$_2$ fragment). Therefore, in some examples, the population of NK cells is contacted with the F(ab')$_2$ fragment of the anti-CD38 antibody at least 1 hour prior to contacting the F(ab')$_2$ fragment-bound NK cells with CD38 expressing cells or prior to administering to a subject. For example, the population of NK cells can be contacted with the F(ab')$_2$ fragment at least 1 hour to 3 weeks (for example, about 2 hours, about 4 hours, about 8 hours, about 12 hours, about 24 hours, about 48 hours, about 3 days, about 4 days, about 5 days, about 6 days, about 7 days, about 10 days, about 14 days, or about 21 days) prior to administration to a subject or contacting with CD38-expressing cells.

In some embodiments, the NK cells that are contacted with the F(ab')$_2$ fragment are autologous NK cells, for example, NK cells from a blood sample from the same subject that is to be treated using the methods described herein. Alternatively, the NK cells are allogeneic, for example, from a different individual that the subject that is to be treated. Allogeneic NK cells may be from a related or unrelated donor and may be either partially or fully HLA-matched.

In some examples, the population of NK cells (for example a population of NK cells from a subject) are collected and used fresh or are collected and cultured for 12-36 hours in growth media or cytokines (such as IL-15 and/or IL-2 or other cytokines) prior to contacting with an anti-CD38 F(ab')$_2$ fragment. In other examples, they are expanded ex vivo prior to contacting with an anti-CD38 F(ab')$_2$ fragment. In some examples, NK cells (such as CD3$^-$CD56$^+$ cells) are expanded by culturing the cells in a suitable cell culture medium (such as X-VIVO™ medium) in the presence of one or more cytokines (for example IL-2) for about 1 to 30 days. Expansion of NK cells can also be done in the presence of feeder cells, such as EBV-LCL cells, K562-mb15-41BBL cells, K562 cells genetically modified to express other molecules to expand NK cells such as membrane bound IL-21, NK-depleted PBMCs, stromal cells, or irradiated tumor cells (such as HFWT). NK cells can also be expanded with cytokines alone without feeder cells in media containing other NK cell growth factors such as nicotinamide. Any feeder cell population used to expand NK cells are first gamma-irradiated prior to their use. Methods of expanding NK cells are known to one skilled in the art (see, e.g., Childs and Berg, *Hematology Am. Soc. Hematol. Educ. Program* 2013:234-246, 2013).

VI. Methods of Treating or Inhibiting a Disorder

Disclosed herein are methods of treating or inhibiting a disorder (such as a hyperproliferative disorder or an autoimmune disorder) that include 1) administering to a subject with the disorder a population of NK cells that are bound to a F(ab')$_2$ fragment of an anti-CD38 antibody and 2) administering to the subject an intact anti-CD38 antibody or a fragment thereof.

In some examples, the methods include treating or inhibiting a hyperproliferative disorder, such as a hematological malignancy or a solid tumor. Examples of hematological malignancies include leukemias, including acute leukemias (such as 11q23-positive acute leukemia, acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), T-cell large granular lymphocyte leukemia, polycythemia vera, lymphoma, diffuse large B-cell lymphoma, Hodgkin's lymphoma, non-Hodgkin's lymphoma (indolent and high grade forms), mantle cell lymphoma, follicular cell lymphoma, multiple myeloma, Waldenstrom's macroglobulinemia, heavy chain disease, myelodysplastic syndrome, hairy cell leukemia and myelodysplasia.

Examples of solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer (including basal breast carcinoma, ductal carcinoma and lobular breast carcinoma), lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytoma, sebaceous gland carcinoma, papillary carcinoma, papillary adenocarcinoma, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyrgioma, ependymoma, pinealoma, hemangioblastoma, acoustic neuroma, oligodendroglioma, meningioma, melanoma, neuroblastoma, and retinoblastoma).

In particular examples, hematological malignancies that can be inhibited or treated by the methods disclosed herein include but are not limited to multiple myeloma, chronic lymphocytic leukemia, acute lymphocytic leukemia, acute myeloid leukemia, chronic myeloid leukemia, pro-lymphocytic/myelocytic leukemia, plasma cell leukemia, NK cell leukemia, Waldenstrom macroglobulinemia, Hodgkin's lymphoma, non-Hodgkin's lymphoma, mantle cell lymphoma, diffuse large B-cell lymphoma, and follicular lymphoma. In additional particular examples, solid tumors that can be treated or inhibited by the methods disclosed herein include lung carcinoma, prostate cancer, pancreatic cancer (for example, insulinoma), breast cancer, colorectal adenocarcinoma or squamous cell carcinoma, neuroblastoma, testicular cancer (such as seminoma), and ovarian cancer. In particular examples, the cells of the hematological malignancy or the solid tumor express or overexpress CD38. In one specific example, the subject has multiple myeloma.

In other examples, the methods disclosed herein may be used to treat autoimmune disorders (such as systemic lupus, rheumatoid arthritis, multiple sclerosis, erythematosus, or asthma. In some examples, the cells that cause or contribute to the autoimmune disorder express CD38. In other examples, the methods disclosed herein may be used to treat any disorder associated with the production of an antibody that leads to disease. For example anti-phospholipid antibody syndrome, lupus, acquired factor VIII inhibitor, antibody mediated pure red cell aplasia, HLA allo-immunization or any disease caused by HLA antibodies such as platelet transfusion refractoriness, to eradicate undesirable antibody populations such as HLA antibodies prior to solid organ or bone marrow or peripheral blood or cord blood transplantation, to eradicate RBC or platelet alloantibodies in patients needing RBC or platelet transfusions or in patients who develop RBC or platelet antibodies after hematopoietic stem cell transplantation leading to RBC transfusion dependence and difficulties finding suitable/compatible RBC or platelet donors.

The methods disclosed herein include treating a disorder (such as a hyperproliferative disorder) in a subject by administering to the subject both an anti-CD38 antibody and a population of NK cells bound to a F(ab')$_2$ fragment of an anti-CD38 antibody. In particular examples, the subject is administered an effective dose of anti-CD38 antibody (such as daratumumab) before, after, or substantially simultaneously with the population of F(ab')$_2$ fragment-bound NK cells. In some examples, the subject is administered about 0.1 mg/kg to about 100 mg/kg of the anti-CD38 antibody (such as about 0.5-10 mg/kg, about 1-20 mg/kg, about 10-50 mg/kg, about 20-100 mg/kg, for example, about 0.5 mg/kg, about 1 mg/kg, about 2 mg/kg, about 3 mg/kg, about 4 mg/kg, about 5 mg/kg, about 8 mg/kg, about 10 mg/kg, about 16 mg/kg, about 20 mg/kg, about 24 mg/kg, about 36 mg/kg, about 48 mg/kg, about 60 mg/kg, about 75 mg/kg, or about 100 mg/kg). An effective amount of the anti-CD38 antibody can be selected by a skilled clinician, taking into consideration the disorder, the general condition of the subject, any additional treatments the subject is receiving or has previously received, and other relevant factors. The subject is also administered a population of NK cells that are bound to the F(ab')$_2$ fragment of an anti-CD38 antibody, for example about $10^4$ to $10^{11}$ NK cells (such as about $10^5$, about $10^6$, about $10^7$, about $10^8$, about $10^9$, about $10^{10}$, or more NK cells). In some examples, about $10^6$ to $10^9$ NK cells/kg (where the NK cells are bound to the F(ab')$_2$ fragment of an anti-CD38 antibody) are administered to a subject. Both the anti-CD38 antibody and the population of NK cells bound to the F(ab')$_2$ fragment are typically administered parenterally, for example intravenously. In other examples, the anti-CD38 antibody and/or the population of NK cells bound to the F(ab')$_2$ fragment are administered locally, for example by injection or infusion to a tumor or close to a tumor. One of skill in the art can determine appropriate routes of administration.

Multiple doses of the population of NK cells bound to the F(ab')$_2$ fragment of the first anti-CD38 antibody and/or the second anti-CD38 antibody can be administered. For example, the population of NK cells bound to the F(ab')$_2$ fragment of the first anti-CD38 antibody can be administered every other day, twice per week, weekly, every other week, every three weeks, monthly, or less frequently. Similarly, the second anti-CD38 antibody can be administered every other day, twice per week, weekly, every other week, every three weeks, monthly, or less frequently. In some examples, the population of NK cells and the second anti-CD38 antibody are administered on the same schedule or on a staggered schedule. A specific example of an administration schedule is provided below; however, a skilled clinician can select alternative schedules based on the subject, the condition being treated, the previous treatment history, and other factors.

The population of NK cells that are bound to the F(ab')$_2$ fragment of the first anti-CD38 antibody is administered to the subject before, after, or substantially simultaneously with the second anti-CD38 antibody. In particular examples, the population of NK cells bound to the F(ab')$_2$ fragment of the first anti-CD38 antibody is administered after the second anti-CD38 antibody, for example within 1 hour to three weeks (such as within about 1-48 hours, about 2-24 hours, about 12-72 hours, about 1-5 days, about 7-21 days, about 10-14 days, for example, within about 2 hours, about 4 hours, about 8 hours, about 12 hours, about 24 hours, about 48 hours, about 3 days, about 4 days, about 5 days, about 6 days, about 7 days, about 10 days, about 14 days, or about 21 days) of the administration of the second anti-CD38 antibody. In one specific example, the population of NK cells bound to the F(ab')$_2$ fragment of the first anti-CD38 antibody is administered to the subject within about 24 hours of the administration of the second anti-CD38 antibody. In some examples, this administration pattern is repeated two times per week for at least two weeks or once weekly for at least two weeks.

In some examples, the subject (such as a subject with a hyperproliferative disorder) is also administered one or more additional treatments, such as one or more chemotherapeutic agents and/or radiation therapy. For example, the subject is treated as described herein, and is also administered an immunomodulatory agent (such as lenalidomide, thalidomide, or pomalidomide), a proteasome inhibitor (such as bortezomib, carfilzomib, salinosporamide A, epoxomicin, marizomib (NPI-0052), ixazomib (MLN9708), CEP18770, or oprozomib (ONX0912)), steroids (such as dexamethasone, prednisone, prednisolone, or methylprednisolone), and/or other chemotherapeutics (such as melphalan). In a particular example, the subject may be administered a combination therapy with the anti-CD38 antibody, such as daratumumab (or another anti-CD38 antibody) in combination with lenalidomide, alone, or in combination with bortezomib. In other examples, the subject may be administered daratumumab (or another anti-CD38 antibody), lenalidomide, bortezomib, and dexamethasone, or daratumumab (or another anti-CD38 antibody), melphalan, prednisone, and bortezomib.

One of skill in the art can select additional chemotherapeutic agents for administration to a subject in combination with the anti-CD38 antibody. Such agents include alkylating agents, such as nitrogen mustards (such as mechlorethamine, cyclophosphamide, melphalan, uracil mustard or chlorambucil), alkyl sulfonates (such as busulfan), nitrosoureas (such as carmustine, lomustine, semustine, streptozocin, or dacarbazine); antimetabolites such as folic acid analogs (such as methotrexate), pyrimidine analogs (such as 5-FU or cytarabine), and purine analogs, such as mercaptopurine or thioguanine; or natural products, for example vinca alkaloids (such as vinblastine, vincristine, or vindesine), epipodophyllotoxins (such as etoposide or teniposide), antibiotics (such as dactinomycin, daunorubicin, doxorubicin, bleomycin, plicamycin, or mitocycin C), and enzymes (such as L-asparaginase). Additional agents include platinum coordination complexes (such as cis-diamine-dichloroplatinum II, also known as cisplatin), substituted ureas (such as hydroxyurea), methyl hydrazine derivatives (such as procarbazine), and adrenocrotical suppressants (such as mitotane and aminoglutethimide); hormones and antagonists, such as adrenocorticosteroids (such as prednisone), progestins (such as hydroxyprogesterone caproate, medroxyprogesterone acetate, and magestrol acetate), estrogens (such as diethylstilbestrol and ethinyl estradiol), antiestrogens (such as tamoxifen), and androgens (such as testosterone proprionate and fluoxymesterone). Examples of the most commonly used chemotherapy drugs include adriamycin, melphalan (Alkeran®) Ara-C (cytarabine), carmustine, busulfan, lomustine, carboplatinum, cisplatinum, cyclophosphamide (Cytoxan®), daunorubicin, dacarbazine, 5-fluorouracil, fludarabine, hydroxyurea, idarubicin, ifosfamide, methotrexate, mithramycin, mitomycin, mitoxantrone, nitrogen mustard, paclitaxel (or other taxanes, such as docetaxel), vinblastine, vincristine, VP-16, while newer drugs include gemcitabine (Gemzar®), trastuzumab (Herceptin®), irinotecan (CPT-11), leustatin, navelbine, rituximab (Rituxan®) imatinib (STI-571), Topotecan (Hycamtin®), capecitabine, ibritumomab (Zevalin®), and calcitriol.

In additional examples, the subject is administered one or more cytokines (such as IL-2, IL-15, IL-21, and/or IL-12) to support survival and/or growth of NK cells. The cytokine(s) can be administered before, after, or substantially simultaneously with the NK cells. In some examples, the cytokine(s) can be administered after the NK cells.

In some examples, administration of the NK cells bound to a F(ab')$_2$ fragment of a first anti-CD38 antibody and a second anti-CD38 antibody to a subject decreases the volume or number of cells of a hematological malignancy (such as MM), a tumor, and/or a metastatic tumor. In addition, the disclosed methods can result in a decrease in the symptoms associated with a hyperproliferative disorder, an increase in survival (including overall survival, progression-free survival and/or metastasis-free survival), or partial or complete remission of disease.

The present disclosure is illustrated by the following non-limiting Examples.

Example 1

NK Cell Killing by Daratumumab is Mediated by CD16

This example describes the effect of daratumumab on NK cells and the role of CD16 in the toxicity of daratumumab to NK cells.

Figure 2B:
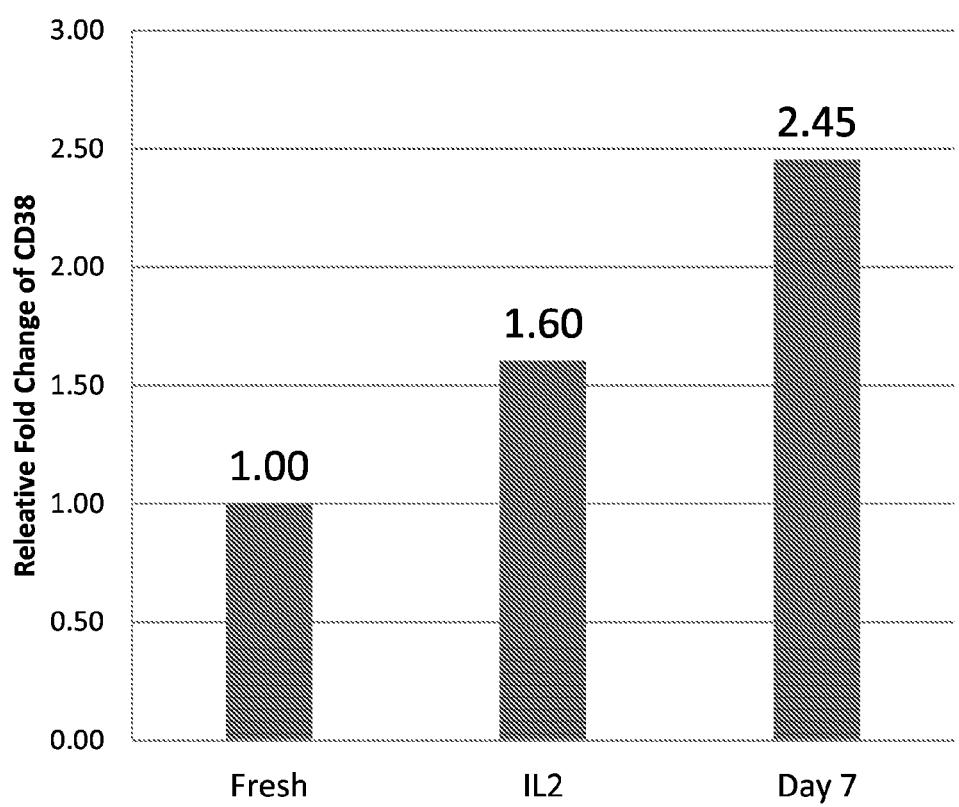

CD38 is expressed on T cells, B cells, NK cells, and myeloma cells (FIG. 1). NK cells were isolated from PBMC using CD3 depletion followed by CD56 selection and were stained with an anti-CD38 antibody or cultured for 18 hours in IL-2 containing media (500 IU/ml) or were expanded ex vivo for 7-14 days in IL-2 containing media (500 IU/ml) using irradiated EBV-LCL feeder cells. The NK cells were then stained with an anti-CD38 antibody. Upon activation and expansion of NK cells in vitro, expression of CD38 increased compared to CD38 expression on resting NK cells, (FIGS. 2A and 2B).

Figure 3A:
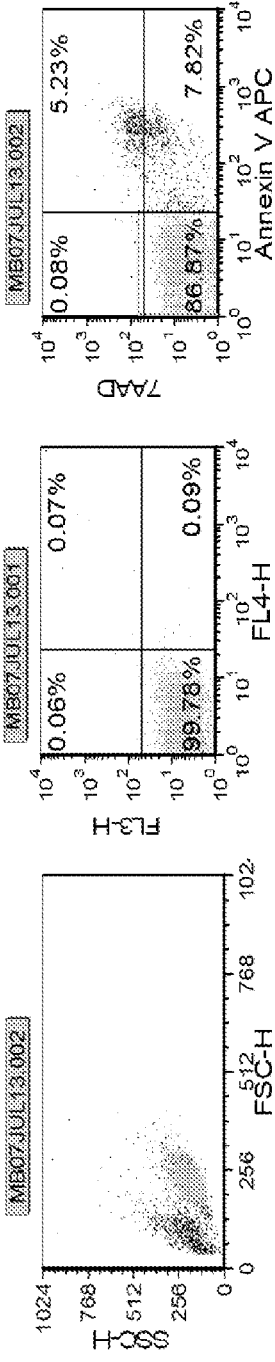
FIGS. 3A-3C are a series of panels showing NK cell viability (measured by Annexin V) in control NK cells (FIG. 3A) or in NK cells incubated with 1 µg/ml daratumumab (FIG. 3B) or 10 µg/ml daratumumab (FIG. 3C).
Figure 3B:
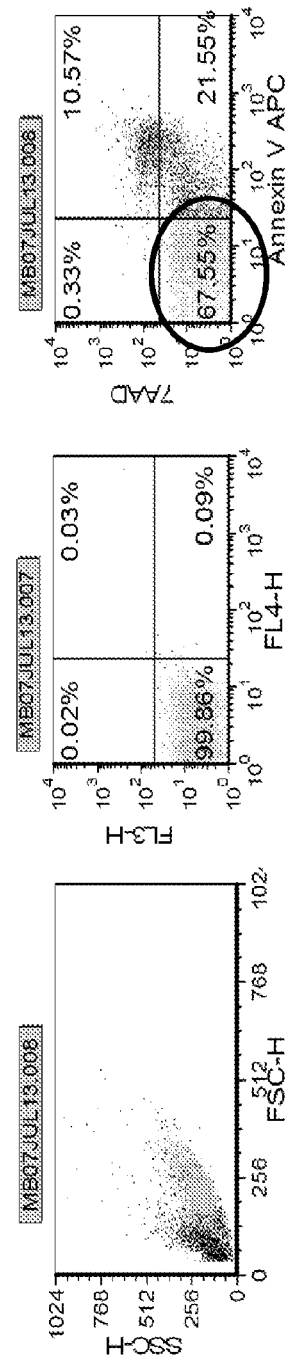
Figure 3C:
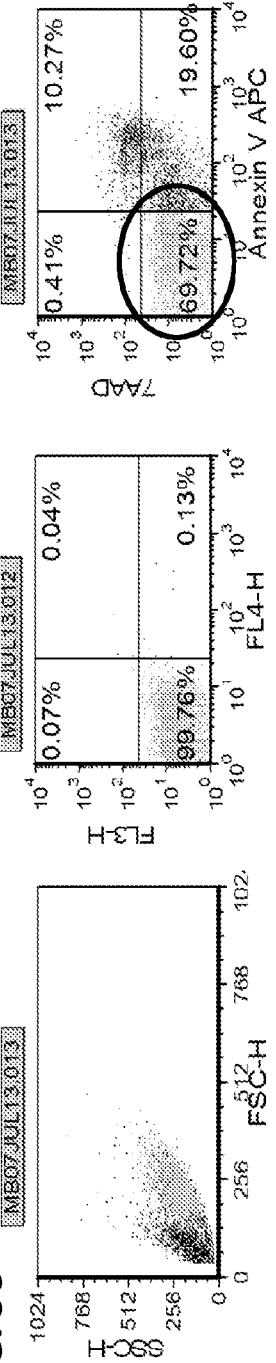

When NK cells which had been expanded as above for 14 days were cultured in media containing daratumumab at a dose of 1 µg/ml (FIG. 3B) or 10 µg/ml (FIG. 3C) for 4 hours, cell viability assessed by staining NK cells with annexin V and 7AAD was decreased compared to control expanded NK cells which were cultured in media without daratumumab. (FIGS. 3A-3C). For example, NK cells were 87% viable in the control population (FIG. 3A), but only 68% and 70% viable when cultured with 1 µg/ml or 10 µg/ml of daratumumab, respectively (FIGS. 3B and 3C).

Figures 5A, 5B:
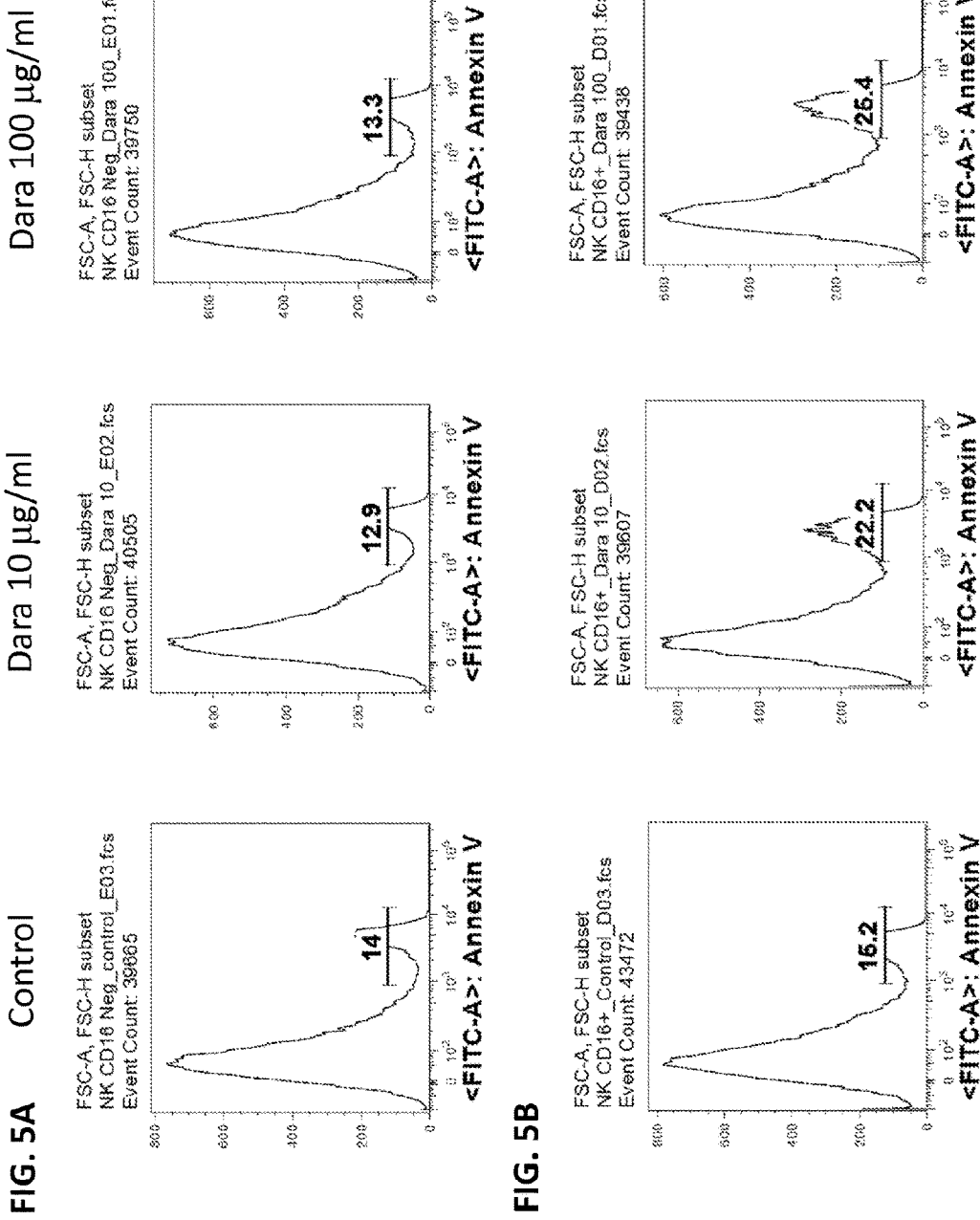
FIGS. 5A and 5B are a series of panels showing the effect of daratumumab on CD16$^-$ (FIG. 5A) or CD16$^+$ (FIG. 5B) NK cell viability in control cells (left panels), 10 µg/ml daratumumab-treated cells (middle panels), and 100 µg/ml daratumumab-treated cells (right panels).

NK cells enriched from PBMC were expanded using EBV-LCL for 14 days as previously described then were sorted using flow cytometry into CD16$^+$ or CD16$^-$ cell populations and CD38 expression was analyzed 48 hours after sorting. CD38 expression was similar on both CD16$^+$ and CD16$^-$ NK cells (FIGS. 4A and 4B). The addition of daratumumab to the media for 4 hours at a concentration of either 10 µg/ml or 100 µg/ml did not have any effect on viability of CD16$^-$ NK cells as assessed by staining for annexin V (FIG. 5A), but did decrease viability of CD16$^+$ NK cells (FIG. 5B). This suggests that CD16 likely mediates NK cell killing by daratumumab through ADCC.

Example 2

Pre-Treating Tumor Cells with Daratumumab Increases NK Cell Killing

This example describes the effect of daratumumab on NK cell killing of tumor cells.

Figure 6A:
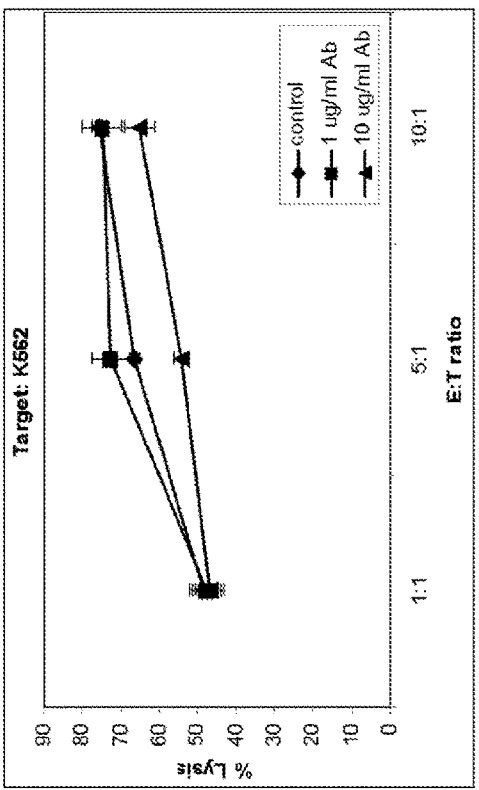
FIGS. 6A-6C are a series of graphs showing % lysis of tumor cell lines in a four hour co-culture of NK cells with 1 µg/ml or 10 µg/ml daratumumab or control cells.
Figure 6C:
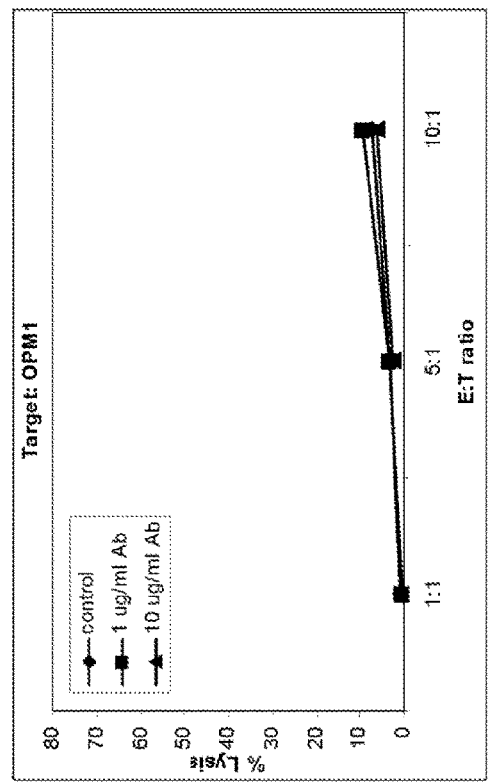
Figure 6B:
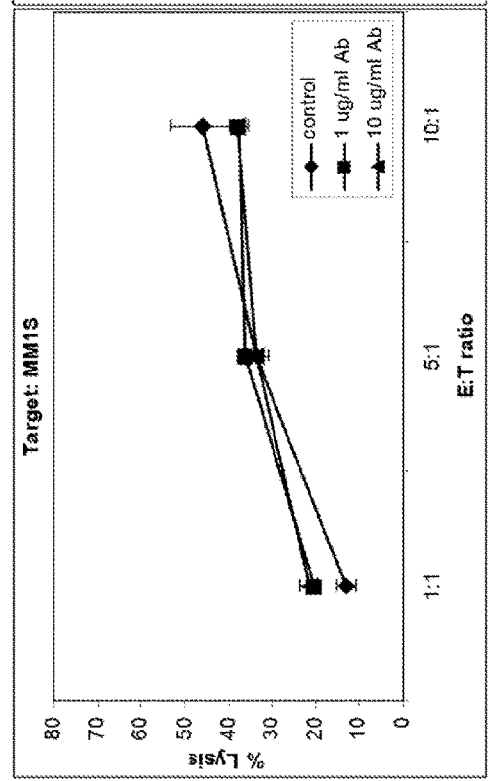

A standard $^{51}$Cr release assay was used to assess the impact of adding daratumumab to media on the effects of NK cell killing of tumor targets. NK cells were expanded for 14 days as described in Example 1 using irradiated EBV-LCL feeder cells. Tumor targets including K562 cells (myelogenous leukemia which is CD38 negative), MM1S cells (multiple myeloma, which is CD38 positive), or OPM1 cells (multiple myeloma, which are CD38 positive) were labeled with $^{51}$Cr then were co-cultured for 5 hours with expanded NK cells in control media without daratumumab or with NK cells in media containing 1 or 10 µg/ml of daratumumab. NK cell effector to tumor target ratios varied between 1:1, 5:1, and 10:1. Adding daratumumab to a co-culture of tumor cells and NK cells had no effect on the lysis of MM1S or OPM1 cells (FIGS. 6B-6C) and actually resulted in a small decrease in K562 cells at the 5:1 E:T ratio (FIG. 6A). However, when daratumumab was added to the tumor cell culture media for 30 minutes at a concentration of 1 or 10 µg/ml of daratumumab, then washed off prior to co-culture with NK cells for 5 hours, a substantial increase in lysis of myeloma cells was observed (FIGS. 7B-7C) and no reduction in NK cell killing of K562 cells (CD38 negative) was observed (FIG. 7A).

Example 3

Effect of CD16 Genotype on Daratumumab-Induced NK Cell Killing

This example describes the effect of high or low affinity CD16 genotype on killing of NK cells by daratumumab.

A single nucleotide polymorphism (SNP rs396991) in CD16 (FcGRIIIA) results in an amino acid substitution at position 158 (V158F). NK cells with the 158V genotype have higher affinity for IgG1 and IgG3 than those with the 158F genotype and exert ADCC more efficiently. DNA was extracted from cryopreserved PBMC from 10 healthy donors and CD16 genotypes were determined using Taq-Man® allelic discrimination. NK cells from four donors were expanded for 14 days using irradiated EBV-LCL feeder cells as previously described. Two donors had high affinity IgG binding genotype (NK D96 and D09) and two had low affinity IgG binding genotype (NK D64 and D136). Day 14 expanded NK cells were cultured in parallel for 2 hours in media with or without daratumumab at a concentration of 10 µg/ml. NK cells from donors with low or high affinity CD16 had similar levels of CD38 expression as assessed by FACS (left panels of figures FIGS. 8A-8B and 9A-9B). The right panels of figures FIGS. 8A-8B and 9A-9B show CD38 staining on NK cells from donors when NK cells were treated with daratumumab at 10 ug/ml for 2 hours, showing the CD38 epitopes were completely bound by the intact daratumumab antibody. Although daratumumab killed both low and high affinity CD16 NK cells, NK cells with low affinity CD16 were less susceptible to daratumumab-induced cell death in the presence of 10 µg/ml daratumumab than NK cells with high affinity CD16 (Table 1).

NK cells from one donor with high affinity IgG binding genotype (NK D96) were flow sorted into CD16$^+$ and CD16$^-$ populations then were cultured for 2 hours in media with daratumumab at a concentration of 10 µg/ml, then were assessed for cell death by staining with annexin V. NK cell killing by daratumumab was shown to be mediated via CD16, as CD16$^-$ NK cells were not killed by daratumumab (FIG. 10A) in contrast to CD16$^+$ NK cells, where substantial NK cell death was observed (FIG. 10B).

TABLE 1

Reduction in NK cell survival in the presence of daratumumab by CD16 genotype

| CD16 Affinity | Control (% viable NK cells) | 10 µg/mL Daratumumab (% viable NK cells) | Reduction in NK Cell Survival Caused by Daratumumab (%) |
| --- | --- | --- | --- |
| Low (D64) | 71.1 | 56.7 | 20 |
| Low (D136) | 77.8 | 69.3 | 11 |

TABLE 1-continued

Reduction in NK cell survival in the presence of daratumumab by CD16 genotype

| CD16 Affinity | Control (% viable NK cells) | 10 µg/mL Daratumumab (% viable NK cells) | Reduction in NK Cell Survival Caused by Daratumumab (%) |
|---|---|---|---|
| High (D09) | 69.3 | 46.6 | 33 |
| High (D96) | 72.7 | 52.4 | 28 |

Figure 12:
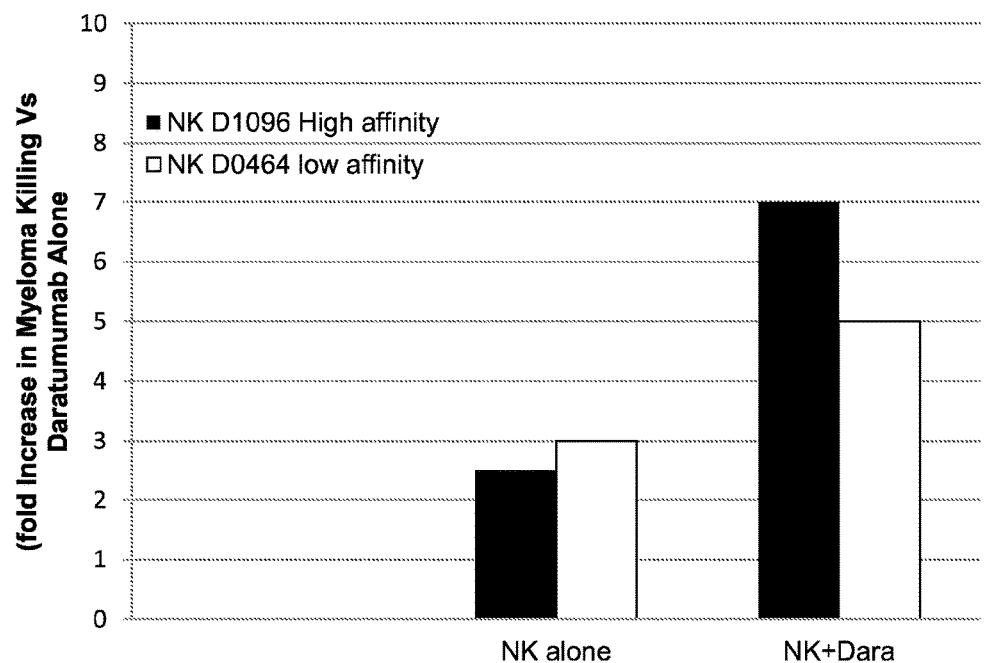
FIG. 12 is a graph showing fold increase in myeloma cell lysis by low or high affinity CD16 NK cells with daratumumab vs. NK cell killing alone without daratumumab.

NK cells expanded from two donors including one with low affinity IgG binding genotype (NK D0464) and one with a high affinity IgG binding genotype (NK D1096) were assessed for cytotoxicity using a standard $^{51}$Cr release assay against a CD38 expressing myeloma line (U226). Myeloma cells were cultured for 5 hours with daratumumab alone or were co-cultured for 5 hours with NK cells alone or were treated for 30 minutes with 10 µg/ml of daratumumab, then were washed and co-cultured with NK cells for 5 hours. NK cell effector to tumor target ratios were 1:1. FIGS. 11A and 11B are graphs showing U226 myeloma cell lysis by low affinity CD16 NK cells (FIG. 11A) or high affinity CD16 NK cells (FIG. 11B) when tumor cells are cultured with daratumumab alone, NK cells alone, or NK cells and daratumumab. Both low and high affinity CD16 NK cells killed U226 myeloma target cells, and this killing was enhanced by daratumumab. However, the high affinity CD16 NK cells showed a greater increase in U226 cell killing than low affinity NK cells (7-fold vs. 5-fold; FIG. 12).

Example 4

Daratumumab F(Ab')$_2$ Inhibits Daratumumab-Mediated Killing of NK Cells

This example describes the effect daratumumab F(ab')$_2$ on NK cell toxicity of daratumumab.

Figure 13:
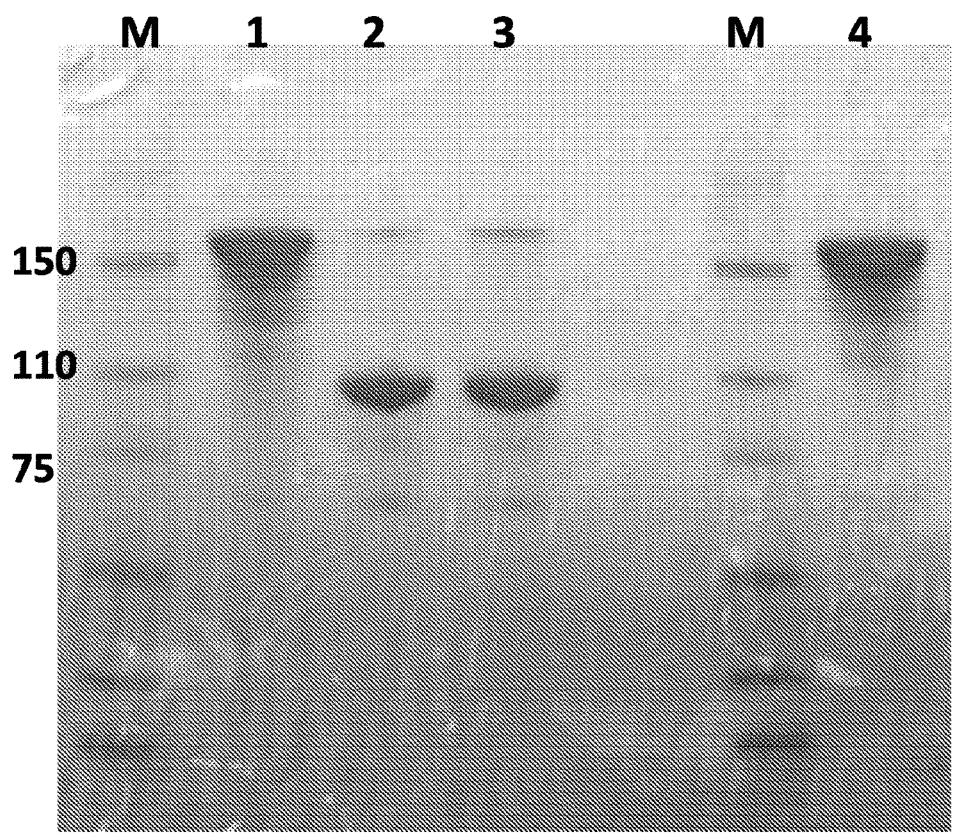
FIG. 13 is a digital image of a Coomassie blue stained gel showing daratumumab or of atumumab F(ab')$_2$ fragments produced using pepsin digestion. M=MW ladder; lane 1=intact daratumumab; lane 2=daratumumab F(ab')$_2$; lane 3=F(ab')$_2$ of atumumab; lane 4=intact of atumumab.
Figure 14C:
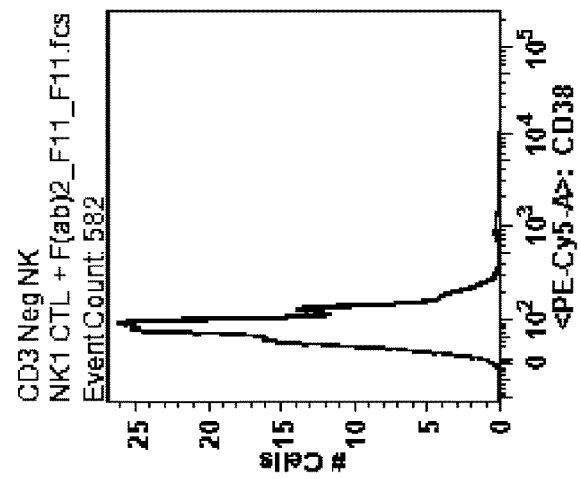
FIGS. 14A-14C are a series of panels showing CD38 staining of NK cells in untreated cells (FIG. 14A), cells treated with daratumumab (FIG. 14B), and cells treated with daratumumab F(ab')$_2$ (FIG. 14C).
Figure 14B:
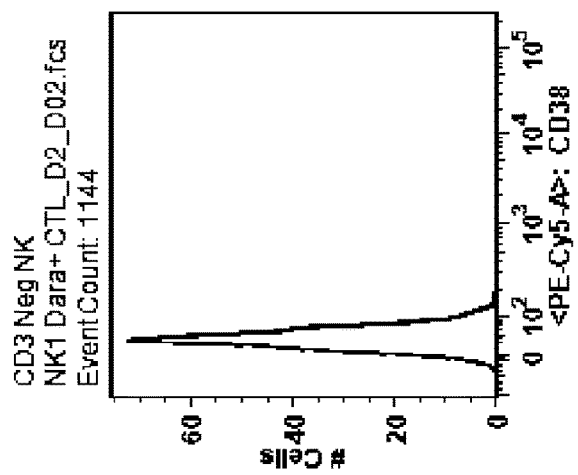
Figure 14A:
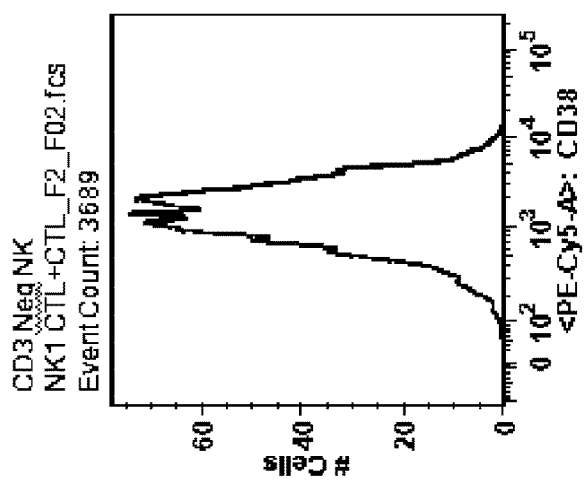

F(ab')$_2$ fragments from daratumumab or of atumumab were generated using a F(ab)$_2$ preparation kit with immobilized pepsin (Thermo Scientific/Pierce, Rockford, Ill.) according to the manufacturer's instructions. The IgG fractions were analyzed by loading 5 µg protein on a non-reducing gel electrophoresis (8-16%) (FIG. 13). Day 10 expanded NK cells were treated with 10 µg/ml of daratumumab F(ab')$_2$ fragments for 30 minutes then were washed and were stained with a PE-conjugated anti-CD38 antibody which bound the same CD38 epitope as the daratumumab antibody. As shown by competition with anti-CD38 PE-Cy5 analyzed by flow cytometry, F(ab')$_2$ fragments blocked CD38 (FIGS. 14A-14C).

Figure 15A:
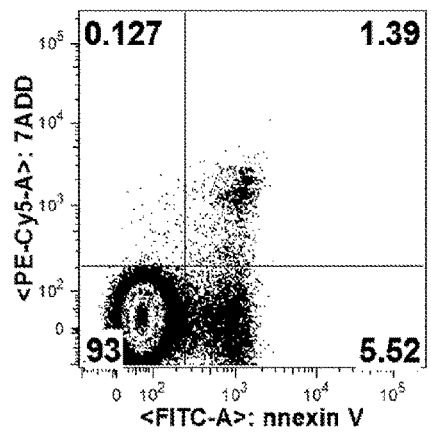
FIGS. 15A-15D are a series of panels showing the effect of daratumumab F(ab')$_2$ fragments on NK cell killing. NK cells from a healthy donor were expanded ex vivo and were untreated (FIG. 15A), treated with 5 μg/ml intact daratumumab (FIG. 15B), or with 5 μg/ml (FIG. 15C) or 10 μg/ml (FIG. 15D) daratumumab F(ab')$_2$. Cell killing was analyzed by flow cytometry with FITC-Annexin V. Viable NK cells are seen in the left lower quadrant of each panel.
Figure 15B:
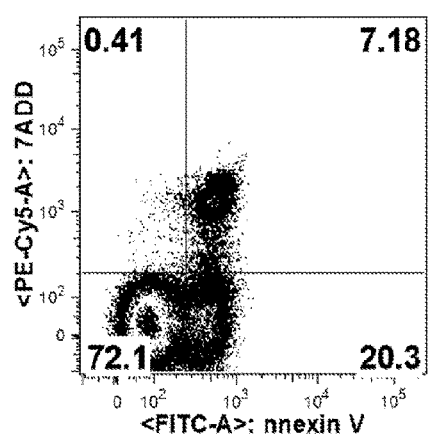
Figure 15C:
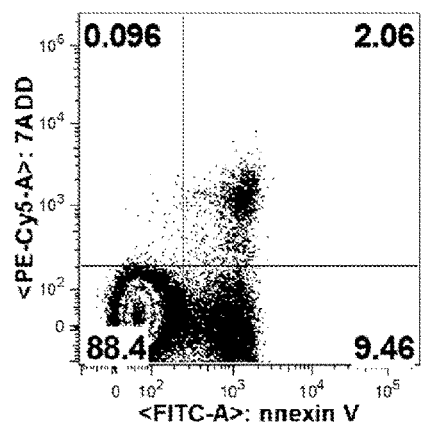
Figure 15D:
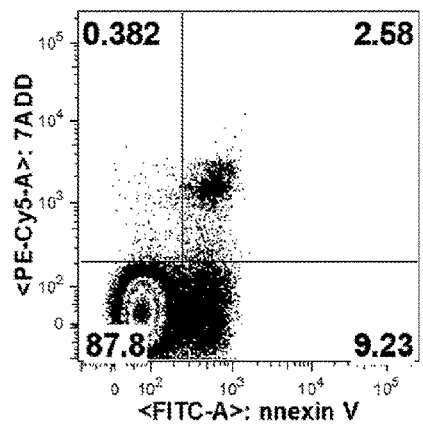

NK cells from a healthy donor were expanded for 10 days using irradiated EBV-LCL feeder cells as previously described. The expanded NK cells were treated for 2 hours with intact daratumumab 5 µg/ml (FIG. 15B), or with 5 µg/ml (FIG. 15C) or 10 µg/ml (FIG. 15D) daratumumab F(ab')$_2$. Cell killing was analyzed by flow cytometry with FITC-Annexin V. Intact daratumumab increased NK cell killing compared to control untreated cells (FIG. 15A); however, daratumumab F(ab')$_2$ did not increase NK cell death (FIGS. 15C and 15D). Viable NK cells are seen in the left lower quadrant of each panel.

Figure 16A:
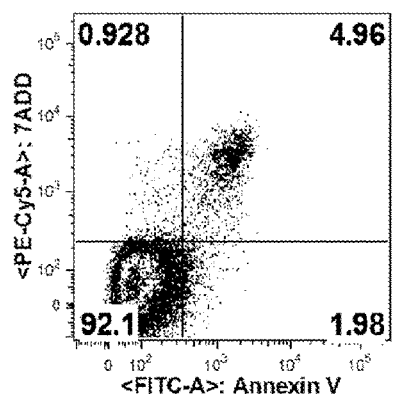
FIGS. 16A-16D are a series of panels showing effect of F(ab')$_2$ antibody fragments on daratumumab-induced apoptosis of NK cells. Daratumumab (FIG. 16B) increased NK cell apoptosis compared to untreated NK cells (FIG. 16A). Daratumumab F(ab')$_2$ inhibited the daratumumab-induced apoptosis of NK cells (FIG. 16C), but F(ab')$_2$ of atumumab did not protect NK cells from daratumumab mediated apoptosis (FIG. 16D).
Figure 16B:
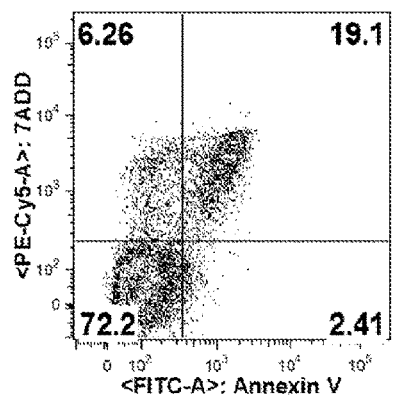
Figure 16C:
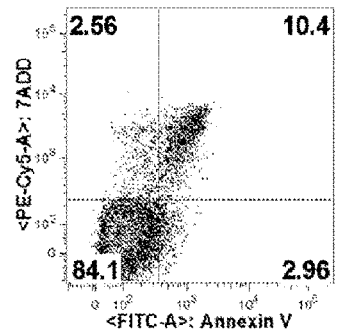
Figure 16D:
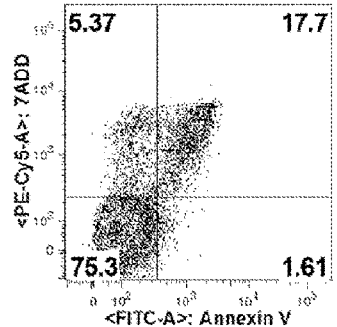

Expanded NK cells (10 days) or the CD16$^-$ NK cell line NK92 were left untreated or treated with F(ab)$_2$ fragments of daratumumab or of atumumab (5 µg/ml in PBS) for 20 minutes at room temperature. The cells were washed and cultured for 2 hours in the presence or absence of intact daratumumab. Cell apoptosis was measured by annexin V and 7ADD staining and flow cytometry. Expanded NK cells were gated as CD3$^-$, CD16$^+$ and CD56$^+$. Daratumumab increased NK cell apoptosis (FIG. 16B) compared to untreated NK cells (FIG. 16A). Pre-treatment of the NK cells with daratumumab F(ab')$_2$ (FIG. 16C) but not F(ab')$_2$ of atumumab (FIG. 16D) prevented the daratumumab-induced apoptosis in NK cells.

Figure 17A:
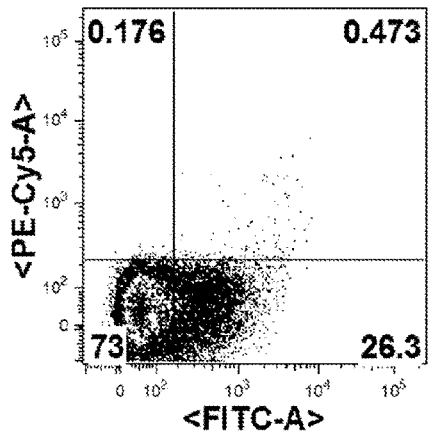
FIGS. 17A-17D are a series of panels showing the effect of daratumumab F(ab')$_2$ fragments on NK cell killing by daratumumab four days after F(ab')$_2$ treatment. NK cells were cultured for four days after treatment with 5 or 10 μg/ml daratumumab F(ab')$_2$ (FIGS. 17A and 17B, respectively), no treatment (FIG. 17C), or treatment with 5 μg/ml F(ab')$_2$ of atumumab (FIG. 17D).
Figure 17B:
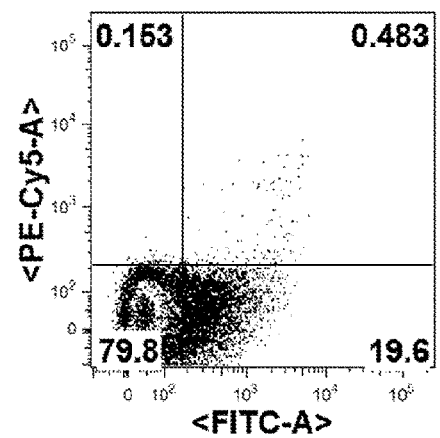
Figure 17C:
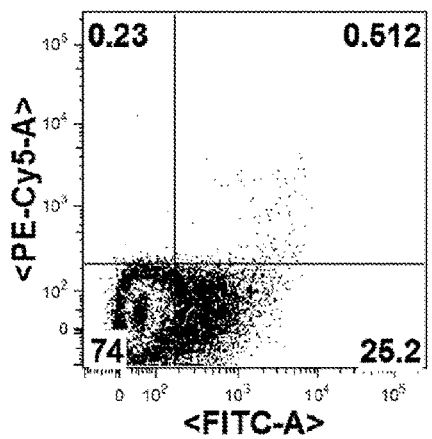
Figure 17D:
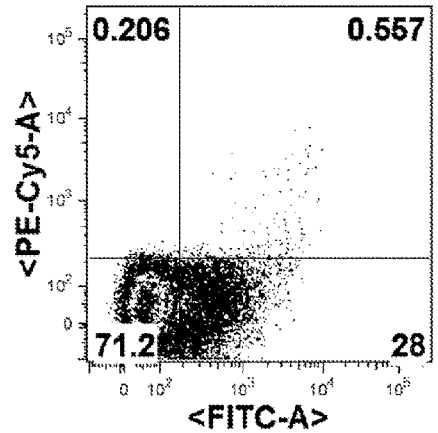

Expanded NK cells (day 21) were left untreated or were treated with F(ab')$_2$ fragments of daratumumab (5 µg/ml or 10 µg/ml in PBS) or of atumumab (5 µg/ml in PBS) for 20 minutes at room temperature. The cells were washed and cultured for 4 days in NK cell complete culture medium without daratumumab. Cell apoptosis was determined as previously described staining for annexin V (FITC) and 7AAD (PE). Treatment of the NK cells with F(ab')$_2$ followed by 4 days of culture did not increase NK cell apoptosis (FIGS. 17A-17B) compared to control NK cells not treated with F(ab')$_2$ (FIG. 17C) or NK cells treated with of atumumab F(ab')$_2$ (FIG. 17D).

Even 4 days after treatment, F(ab')$_2$ daratumumab decreased intact daratumumab-induced apoptosis of NK cells while F(ab')$_2$ of atumumab had no effect. NK cells were left untreated for 4 days (FIG. 18A), or were treated with of atumumab F(ab')$_2$ (FIG. 18B), or daratumumab F(ab')$_2$ (FIG. 18C), then were washed and cultured for 4 days and then had intact daratumumab at a concentration of 10 µg/ml added to the media for 2 hours. Viable NK cells (left lower quadrant of each panel) were greatest among daratumumab F(ab')$_2$ pre-treated NK cells (FIG. 18C).

Example 5

Tumor Cell Lysis by NK Cells Pre-Treated with Daratumumab F(Ab')$_2$

This example describes the effect of NK cells pre-treated with daratumumab F(ab')$_2$ on tumor cell lysis in the presence of daratumumab.

Figure 19:
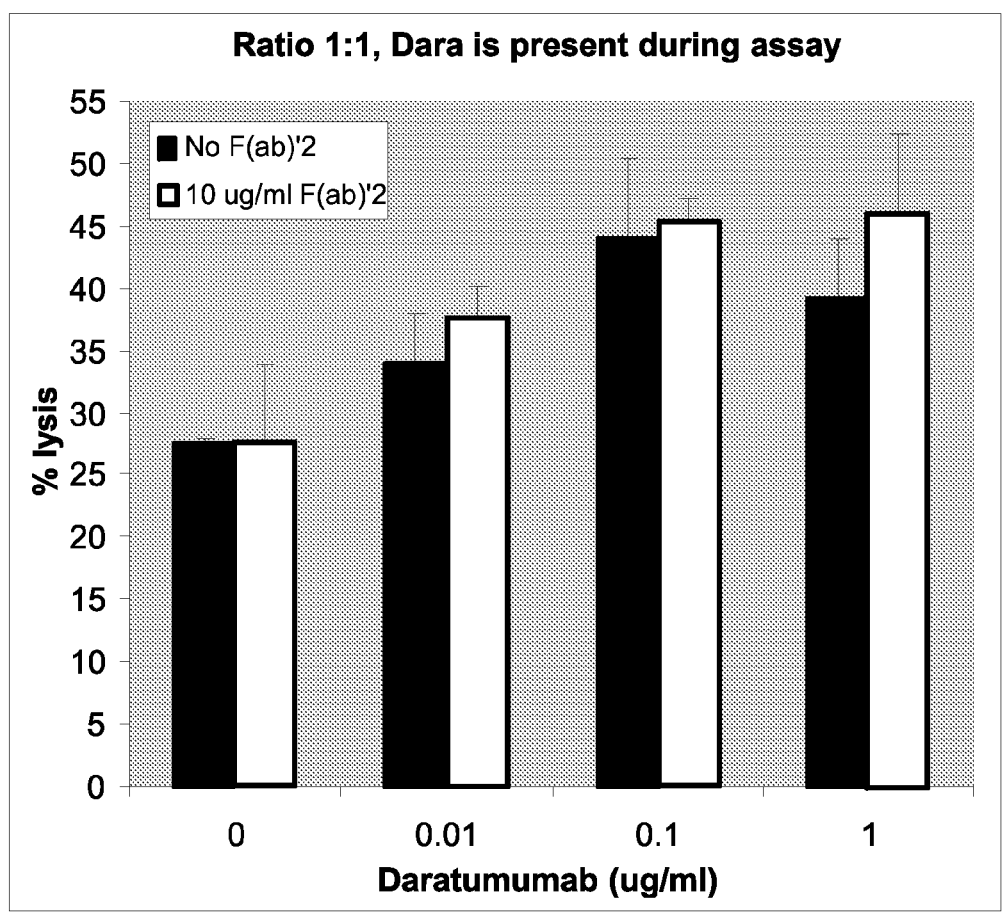
FIG. 19 is a graph showing the effect of NK cells treated with or without daratumumab F(ab')$_2$ on myeloma cell lysis in the presence of 0-1 μg/ml daratumumab.
Figure 20:
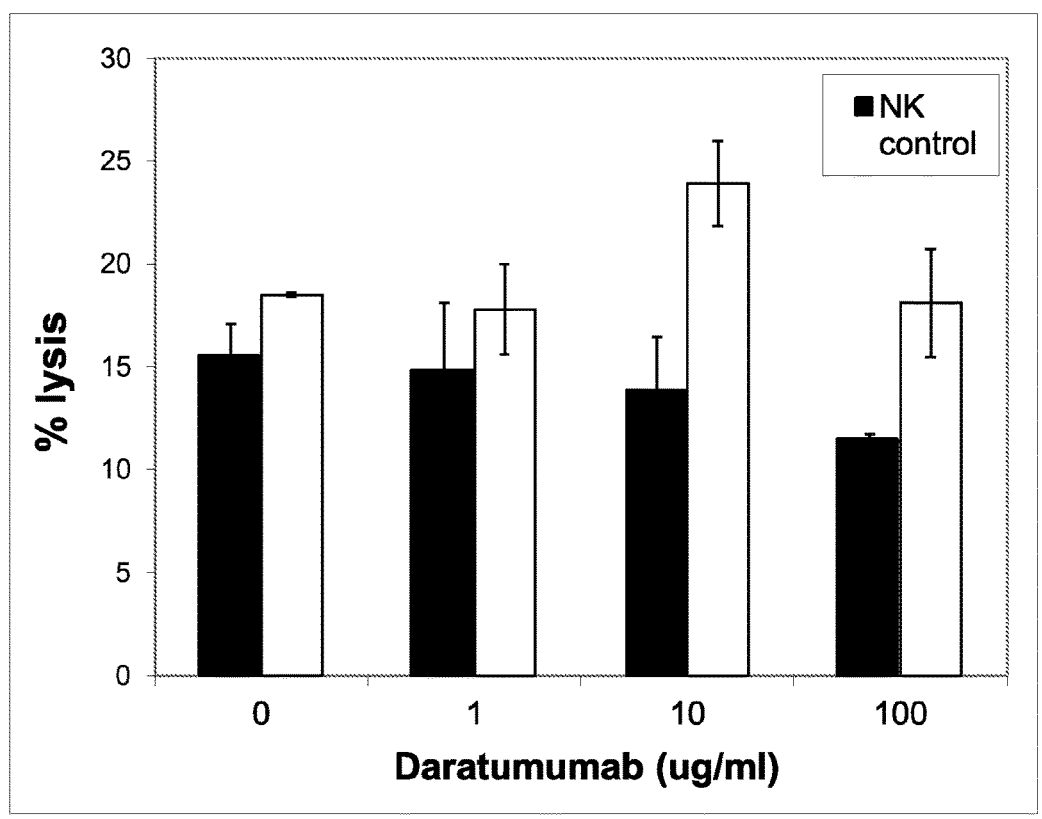
FIG. 20 is a graph showing the effect of NK cells treated with (light gray bars) or without (dark gray bars) daratumumab F(ab')$_2$ on myeloma cell lysis in the presence of 1-100 μg/ml daratumumab.

Myeloma cells (MM1S cells) were exposed to varying concentrations (0 to 1 µg/ml) of intact daratumumab for 30 minutes then were washed and labeled with $^{51}$Cr for cytotoxicity assays. NK cells expanded for 14 days using irradiated EBV-LCL feeder cells were pre-treated with daratumumab F(ab')$_2$ for 30 minutes then were washed and added to the culture medium at a 1:1 ratio with the $^{51}$Cr labeled myeloma cells. Intact daratumumab at concentrations (0 to 1 µg/ml) was added to the media during the co-culture with NK cells. At low concentrations of intact daratumumab in the media (0.01 or 0.1 µg/ml), NK cell killing of the myeloma cells was potentiated (FIG. 19). A slight reduction in NK cell killing was observed at 1 µg/ml intact daratumumab in the media with non-F(ab')$_2$ pre-treated NK cells. This may have been due to killing of NK cells at this concentration of daratumumab. However, NK cell killing was not reduced with F(ab')$_2$ pre-treated cells at the 1 µg/ml daratumumab concentration (FIG. 19), suggesting that the NK cells may have been protected from daratumumab-induced killing by the presence of the F(ab')$_2$. When the same experiment was repeated using higher concentrations of intact daratumumab (10 or 100 µg/ml), NK cell lysis by NK cells that were not treated with daratumumab F(ab')$_2$ decreased in contrast to daratumumab F(ab')$_2$ (FIG. 20).

Example 6

Efficacy of NK Cells Treated with Daratumumab F(ab')$_2$ Fragment in a Mouse Tumor Model This example describes methods for testing the efficacy of treating a tumor with daratumumab F(ab')$_2$-treated NK cells in an animal tumor model system. However, one skilled in the art will appreciate that methods that deviate from these specific methods can also be used to successfully treat a tumor in an animal model.

Immuno-deficient mice (such as NSG mice) are injected in the tail vein with 1 million luciferase transduced MM1S myeloma tumor cells which are CD38+. Tumor cells home to the bone marrow within 72 hours and can be repeatedly imaged using bioluminescent imaging (BLI) to quantitate tumor bulk. Tumors are allowed to become established for 1 week, then mice are divided into the following cohorts. Cohort 1 receives saline alone i.p. Cohort 2 receives a single i.p. injection of daratumumab at a dose of 20 μg. Cohort 3 receives 5 million human NK cells i.v. which have been expanded in vitro for 14 days using EBV-LCL feeder cells as previously described. Cohort 4 receives 5 million human NK cells i.v. which have been expanded in vitro for 14 days using EBV-LCL feeder cells as previously described which are treated with F(ab')$_2$ fragments of daratumumab (5 μg/ml in PBS) for 20 minutes at room temperature then washed and infused into mice. Cohort 5 receives a single i.p. injection of daratumumab at a dose of 20 μg followed 2 hours later by a single injection of 5 million human NK cells which have been expanded in vitro for 14 days using EBV-LCL feeder cells as previously described. Cohort 6 receives a single i.p. injection of daratumumab at a dose of 20 μg followed 2 hours later by a single injection of 5 million human NK cells which have been expanded in vitro for 14 days using EBV-LCL feeder cells as previously described and which are treated with F(ab')$_2$ fragments of daratumumab (5 μg/ml in PBS) for 20 minutes at room temperature then washed and infused into the mice. All mice cohorts are weighed twice weekly and undergo twice weekly BLI imaging to quantitate the bulk of their tumors and are followed for survival.

Example 7

Treatment of a Subject with Multiple Myeloma with NK Cells Treated with Daratumumab F(Ab')$_2$ and Intact Daratumumab This example describes exemplary methods for adoptive transfer of daratumumab F(ab')$_2$ fragment-treated NK cells, for example for treatment of multiple myeloma. However, one skilled in the art will appreciate that methods that deviate from these specific methods can also be used to successfully for adoptive transfer and treatment of multiple myeloma or other malignancies.

Subjects with multiple myeloma are identified, for example, using standard diagnostic criteria. In some examples, some subjects may be treated with daratumumab alone or in combination with standard chemotherapeutics while other subjects are treated with NK cells bound to daratumumab F(ab')$_2$ fragment and intact daratumumab.

Purified NK cells are obtained either from the subject or a donor. The NK cells are expanded ex vivo using irradiated EBV-LCL feeder cells as previously described. Following a 14-21 day ex vivo expansion, $10^8$ NK cells/kg are treated with 1-20 μg/ml daratumumab F(ab')$_2$ fragment for 10-60 minutes at room temperature. The NK cells are then washed to remove unbound F(ab')$_2$ fragment and are resuspended at a concentration of 50 million NK cells/ml in PBS containing either autologous plasma (1-10%) or human serum albumin.

Intact daratumumab (2-24 mg/kg) is administered intravenously to the subject with multiple myeloma. Within 24 hours, $10^8$ NK cells/kg from the preparation of NK cells bound to the daratumumab F(ab')$_2$ fragment is administered intravenously to the subject. Treatment with intact daratumumab followed within 24 hours with NK cells bound to the daratumumab F(ab')$_2$ fragment is repeated weekly for at least 3 weeks.

Following the administration, subjects can be monitored for reductions in one or more clinical symptoms associated with multiple myeloma. In particular examples, subjects are analyzed one or more times, starting 7 days following treatment. Subjects can be monitored using any method known in the art. For example, serum or urine M protein levels or kappa or lambda free light chains of the subject can be assessed. Other signs and symptoms of multiple myeloma can also be assessed, such as blood calcium levels, bone marrow plasma cell percentage, or presence or size of bone lesions or plasmacytomas. A reduction in one or more clinical symptoms associated with multiple myeloma, for example, reduced M protein levels, indicates the effectiveness of the treatment.

One of skill in the art will appreciate that the disclosed agents including NK cells bound to daratumumab F(ab')$_2$ fragment can be tested for safety in animals, and then used for clinical trials in animals or humans. In one example, animal models of cancer are employed to determine therapeutic value and/or dosages of the disclosed agents.

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. A method of inhibiting growth or proliferation of CD38-expressing cells, comprising:
    contacting a population of natural killer (NK) cells with a F(ab')$_2$ fragment of a first anti-CD38 antibody, thereby producing a population of NK cells bound to the F(ab')$_2$ fragment of the first anti-CD38 antibody; and
    contacting a population of CD38-expressing cells with a second anti-CD38 antibody and the population of NK cells bound to the F(ab')$_2$ fragment of the first anti-CD38 antibody, thereby inhibiting growth or proliferation of the CD38-expressing cells.

2. The method of claim 1, wherein the F(ab')$_2$ fragment of the first anti-CD38 antibody comprises the F(ab')$_2$ fragment of a human anti-CD38 antibody or a humanized anti-CD38 antibody and/or wherein the second anti-CD38 antibody comprises a human anti-CD38 antibody, a humanized anti-CD38 antibody, or a fragment thereof.

3. The method of claim 2, wherein the first anti-CD38 antibody and/or the second anti-CD38 antibody comprise daratumumab or SAR650984.

4. The method of claim 1, wherein the first anti-CD38 antibody and the second anti-CD38 antibody are the same.

5. The method of claim 1, wherein the population of NK cells comprises CD16 positive and/or CD56 positive NK cells.

6. The method of claim 1, wherein contacting the population of NK cells with the F(ab')$_2$ fragment of the first anti-CD38 antibody occurs in vitro or ex vivo and/or contacting the population of CD38-expressing cells with the second anti-CD38 antibody and the population of NK cells bound to the ab')$_2$ fragment of the first anti-CD38 antibody occurs in vivo, in vitro, or ex vivo.

7. The method of claim 6, further comprising expanding the population of NK cells in vitro or ex vivo prior to contacting the population of NK cells with the F(ab')$_2$ fragment of the first anti-CD38 antibody.

8. The method of claim 6, wherein contacting the population of CD38-expressing cells with the second anti-CD38 antibody and the population of NK cells bound to the F(ab')$_2$ fragment of the first anti-CD38 antibody comprises administering the second anti-CD38 antibody and the population of NK cells bound to the F(ab')$_2$ fragment of the first anti-CD38 antibody to a subject with a disorder comprising CD38-expressing cells.

9. The method of claim 8, wherein administering the population of NK cells bound to the F(ab')$_2$ fragment of the first anti-CD38 antibody to the subject occurs before, after, or substantially simultaneously with administering the second anti-CD38 antibody to the subject.

10. The method of claim 1, wherein the CD38-expressing cells comprise CD38-expressing cancer cells or CD38-expressing T-cells, B-cells, NK cells, or plasma cells.

11. The method of claim 10, wherein the CD38-expressing cancer cells comprise solid tumor cells or hematological malignancy cells.

12. The method of claim 11, wherein the hematological malignancy cells comprise multiple myeloma cells, acute lymphocytic leukemia cells, acute myeloid leukemia cells, chronic lymphocytic leukemia cells, chronic myeloid leukemia cells, Hodgkin's lymphoma cells, non-Hodgkin's lymphoma cells, T-LGL leukemia cells, NK cell leukemia cells, or hairy cell leukemia cells.

13. A method of treating or inhibiting a hyperproliferative disorder or an autoimmune disorder in a subject, comprising:
   administering to the subject an effective amount of a population of natural killer (NK) cells bound to a F(ab')$_2$ fragment of a first anti-CD38 antibody; and
   administering to the subject an effective amount of a second anti-CD38 antibody, wherein the second anti-CD38 antibody is administered to the subject before, after, or substantially simultaneously with administering the population of natural killer (NK) cells bound to a F(ab')$_2$ fragment of a first anti-CD38 antibody, thereby treating or inhibiting the hyperproliferative disorder.

14. The method of claim 13, wherein the F(ab')$_2$ fragment of the first anti-CD38 antibody comprises the F(ab')$_2$ fragment of a human anti-CD38 antibody or a humanized anti-CD38 antibody and/or wherein the second anti-CD38 antibody comprises a human anti-CD38 antibody, a humanized anti-CD38 antibody, or a fragment thereof.

15. The method of claim 14, wherein the first anti-CD38 antibody and/or the second anti-CD38 antibody comprise daratumumab or SAR650984.

16. The method of claim 13, wherein the first anti-CD38 antibody and the second anti-CD38 antibody are the same.

17. The method of claim 13, wherein the population of NK cells comprises CD16 positive and/or CD56 positive NK cells.

18. The method of claim 13, wherein the population of NK cells bound to the F(ab')$_2$ fragment of the first anti-CD38 antibody is produced in vitro or ex vivo by contacting a population of natural killer (NK) cells with the F(ab')$_2$ fragment of the first anti-CD38 antibody.

19. The method of claim 18, further comprising expanding the population of NK cells in vitro or ex vivo prior to contacting the population of NK cells with the F(ab')$_2$ fragment of the first anti-CD38 antibody.

20. The method of claim 13, wherein the population of NK cells comprises autologous NK cells or allogeneic NK cells.

21. The method of claim 13, wherein the hyperproliferative disorder comprises a solid tumor or a hematological malignancy.

22. The method of claim 21, wherein the hematological malignancy comprises multiple myeloma, acute lymphocytic leukemia, acute myeloid leukemia, chronic lymphocytic leukemia, chronic myeloid leukemia, Hodgkin's lymphoma, or non-Hodgkin's lymphoma.

23. The method of claim 21, wherein the cells of the solid tumor or the hematological malignancy express CD38.

24. A method of treating or inhibiting a hyperproliferative disorder in a subject comprising:
   contacting a population of NK cells isolated from the subject with a F(ab')$_2$ fragment of a first anti-CD38 antibody to produce a population of NK cells bound to the F(ab')$_2$ fragment of the first anti-CD38 antibody;
   administering to the subject a therapeutically effective amount of a second anti-CD38 antibody or fragment thereof; and
   administering to the subject the population of NK cells bound to the F(ab')$_2$ fragment of the first anti-CD38 antibody, thereby treating or inhibiting the hyperproliferative disorder.

25. A pharmaceutical composition comprising a population of natural killer (NK) cells bound to a F(ab')$_2$ fragment of an anti-CD38 antibody and a pharmaceutically acceptable carrier.

26. The pharmaceutical composition of claim 25, wherein the F(ab')$_2$ fragment of the anti-CD38 antibody comprises a F(ab')$_2$ fragment of a human anti-CD38 antibody or a humanized anti-CD38 antibody.

27. The pharmaceutical composition of claim 25, wherein the anti-CD38 antibody comprises daratumumab or SAR650984.

* * * * *